United States Patent [19]

Camaggi et al.

[11] Patent Number: 5,556,829
[45] Date of Patent: *Sep. 17, 1996

[54] COMPOSITIONS HAVING HERBICIDAL ACTIVITY CONTAINING N-ALKYL-AMIDES AS ACTIVE INGREDIENT

[75] Inventors: Giovanni Camaggi, Novara; Dario Chiarino, Monza; Mario Fantucci, Milan; Giovanni Meazza, Saronno, all of Italy

[73] Assignees: Zambon Group S.p.A., Vicenza; Agrimont S.p.A., Milan, both of Italy

[*] Notice: The term of this patent shall not extend beyond the expiration date of Pat. No. 5,336,664.

[21] Appl. No.: 250,619

[22] Filed: May 27, 1994

Related U.S. Application Data

[63] Continuation of Ser. No. 688,828, Apr. 22, 1991, Pat. No. 5,336,664.

[30] Foreign Application Priority Data

Apr. 24, 1990 [IT] Italy ..................................... 20130/90

[51] Int. Cl.$^6$ ............................. A01N 57/06; A01N 57/08
[52] U.S. Cl. ........................ 504/199; 504/209; 504/221; 504/223; 504/224; 504/235; 504/239; 504/244; 504/248; 504/261; 504/270; 504/279; 504/283; 504/287; 504/288; 504/291; 504/299; 504/333
[58] Field of Search ..................................... 504/333, 209, 504/221, 223, 235, 244, 261, 283, 288, 291, 199, 249, 289, 239, 288, 248, 224, 287, 279, 273, 261, 291, 270; 564/212, 213; 574/628

[56] References Cited

U.S. PATENT DOCUMENTS

| | | | |
|---|---|---|---|
| 2,717,268 | 9/1955 | Rebstock et al. | 564/213 |
| 2,734,919 | 2/1956 | Amiard et al. | 564/304 |
| 2,742,500 | 4/1956 | Gregory et al. | 564/86 |
| 2,759,970 | 8/1956 | Suter | 564/212 |
| 2,759,972 | 8/1956 | Suter | 564/212 |
| 2,816,915 | 12/1957 | Gregory | 562/401 |
| 4,235,892 | 11/1980 | Nagabhushan | 564/212 |
| 4,632,940 | 12/1986 | Chiarino et al. | 514/648 |
| 4,638,003 | 1/1987 | Chiarino et al. | 514/255 |
| 4,743,700 | 5/1988 | Jommi et al. | 548/216 |
| 5,336,664 | 8/1994 | Camaggi et al. | 504/261 |

FOREIGN PATENT DOCUMENTS

| | | |
|---|---|---|
| 0000051 | 12/1978 | European Pat. Off. . |
| 0014437 | 8/1980 | European Pat. Off. . |
| 0130633 | 1/1985 | European Pat. Off. . |
| 0174720 | 3/1986 | European Pat. Off. . |
| 0303934 | 2/1989 | European Pat. Off. . |
| 0323846 | 7/1989 | European Pat. Off. . |
| 0332387 | 9/1989 | European Pat. Off. . |
| 1096234 | 6/1955 | France . |
| 2454805 | 5/1975 | Germany . |
| 699808 | 11/1953 | United Kingdom . |
| 705711 | 3/1954 | United Kingdom . |
| 709595 | 5/1954 | United Kingdom . |
| 743446 | 1/1956 | United Kingdom . |
| 746016 | 3/1956 | United Kingdom . |
| 745900 | 3/1956 | United Kingdom . |
| 746015 | 3/1956 | United Kingdom . |
| 770277 | 3/1957 | United Kingdom . |

OTHER PUBLICATIONS

Grumbach et al "The effect of phytochrome and protein synthesis inhibitors . . . " etc, CA93(7):63466x, 1980.
Grumbach et al "The Effect of Phytochrome . . . ", Z. Naturforsch 35c, pp. 445–450, 1980.
Cutler et al., J. Am. Chem. Soc., 74, 5475 (1952).
Suter et al, J. Am. Chem. Coc., 75, 4330 (1953).
Rebstock et al, J. Am. Chem. Soc., 77, 186, (1955).
Portelli et al., Ann. Chim., 59, 306 (1969).
Portelli et al., Ann. Chim., 60, 160 (1970).
Portelli et al., Ann. Chim, 57, 1018, (1967).
V. Horak et al., Synthesis, 839 (1984).
Chemical Abstracts, vol. 80, No. 11, 18 Mar. 1974, p. 335, Abstract No. 59684f.
Chemical Abstracts, vol. 77, No. 17, 23 Oct. 1972, p. 417 Abstract No. 114021c.
Chemical Abstracts, vol. 95, No. 5, 3 Aug. 1981, p. 213 Abstract No. 36962r.
Chemical Abstracts, vol. 85, No. 15, 11 Oct. 1976, p. 367 Abstract No. 107466p.
Chemical Abstracts, vol. 95, No. 1, 6 Jul. 1981, p. 633 Abstract No. 6676h.

*Primary Examiner*—Peter O'Sullivan
*Assistant Examiner*—Brian G. Bembenick
*Attorney, Agent, or Firm*—Watson Cole Stevens Davis, P.L.L.C.

[57] ABSTRACT

Compounds of formula

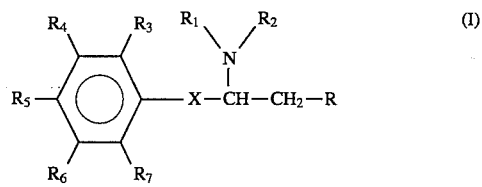

wherein R, $R_1$, $R_2$, $R_3$, $R_4$, $R_5$, $R_6$, $R_7$ and X have the meanings reported in the description, can be used in compositions for agricultural use in particular as herbicides in the defense of useful crops from weeds.

13 Claims, No Drawings

COMPOSITIONS HAVING HERBICIDAL ACTIVITY CONTAINING N-ALKYL-AMIDES AS ACTIVE INGREDIENT

This is a continuation of application Ser. No. 07/688,828, filed Apr. 22, 1991, now U.S. Pat. No. 5,336,664.

The present invention concerns herbicides for agricultural use and more particularly it concerns the use as herbicides of certain N-alkyl-amides variously substituted on the alkyl and composition of agricultural use containing them.

We have surprisingly found, and this constitutes the object of the present invention, that certain N-alkyl-amides variously substituted on the alkyl are endowed with herbicidal activity and can be used in compositions for agricultural use in the defense of useful crops from weeds and in the weed control.

In particular, the above mentioned amides endowed with herbicidal activity have the following general formula

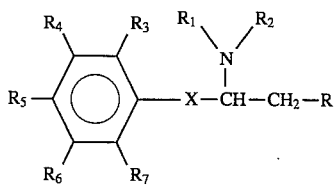

(I)

wherein

R is a hydrogen atom, alkyl, hydroxy, alkoxy, a fluorine, chlorine or bromine atom, a cyano group, alkylcarbonyloxy, alkylcarbonylthio, mercapto or alkylthio;

when one of $R_1$ and $R_2$ is a hydrogen atom or a $C_1$–$C_3$ alkyl and the other is a group

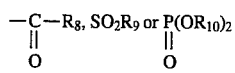

wherein $R_8$ is a hydrogen atom, alkoxy, aminocarbonyl, carboxy, alkoxycarbonyl, alkylcarbonyl, alkyl optionally substituted by from 1 to 3 substituents selected among fluorine, chlorine or bromine atoms, hydroxy, cyano, alkoxy, mercapto, $C_3$–$C_6$ cycloalkyl optionally substituted by 1 or 2 chlorine atoms, amino, mono or dialkylamino, formylamino, aminocarbonyl, alkylthio, alkylsulfinyl, alkylsulfonyl, hydroxyimino, alkoxyimino, carboxy, alkoxycarbonyl, alkylcarbonyloxy, tetrazolyl, alkylcarbonyl, phenyl and azido; $C_2$–$C_6$ alkylene optionally substituted by 1 or 2 fluorine or chlorine atoms or alkoxy; a $C_2$–$C_6$ alkynyl; a $C_3$–$C_6$ cycloalkyl; a heterocycle with 3–6 atoms among which 1 or 2 are heteroatoms selected among oxygen, nitrogen and sulfur; $R_9$ is alkyl, mono or dichloroalkyl, phenyl optionally substituted by from 1 to 3 fluorine, chlorine or bromine atoms or alkyl; the $R_{10}$s are hydrogen atoms or alkyls;

$R_3$, $R_4$, $R_5$, $R_6$ and $R_7$, equal to or different from each other, each are a hydrogen, fluorine, chlorine or bromine atom, trifluoromethyl, alkyl, alkoxy, hydroxy, alkylthio, alkylsulfinyl, alkylsulfonyl, wherein alkyl is optionally substituted by from 1 to 3 fluorine, chlorine or bromine atoms; $C_2$–$C_6$ alkenylthio, benzylthio, $C_2$–$C_6$ alkenylsulfinyl, $C_2$–$C_6$ alkenylsulfonyl; benzylsulfinyl, benzylsulfonyl, benzenesulfonyl; cyano, alkylcarbonyl, alkylcarbonylamino; amino, mono or dialkylamino, trifluoroacetylamino, alkylsulfonylamino, benzoylamino wherein the phenyl may be substituted by from 1 to 3 substituents selected among fluorine, chlorine or bromine atoms or alkyls, or one of $R_3$, $R_4$, $R_5$, $R_6$ and $R_7$ is a phenyl, phenoxy, pyridyloxy, such groups being optionally substituted by from 1 to 3 substituents selected among fluorine, chlorine or bromine atoms, alkyl or alkoxy groups;

X is a

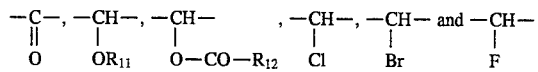

wherein $R_{11}$ is a hydrogen atom, alkyl, acyl of a mineral acid selected among nitric, phosphoric and sulfuric acid or an acyl of alkylsulfonic or benzenesulfonic acid; $R_{12}$ is hydrogen atom, alkyl optionally substituted by from 1 to 3 substituents selected among fluorine, chlorine or bromine atoms, alkoxy or cyano; phenyl optionally substituted by from 1 to 3 substituents selected among fluorine, chlorine or bromine atoms, alkyl, nitro, alkoxy; a $C_2$–$C_6$ alkenyl;

and their salts with organic or inorganic acids compatible with agrarian use.

Some of the compounds of formula I are new and as such they constitute another object of the present invention. Among these, in particular, the compounds of formula I wherein $R_8$ represents a cyanomethyl or a hydrogen atom.

Independently from conventions of chemical nomenclature, which may modify from time to time the system of numbering, in the instant context we indicate as (b) the carbon atom bonded to the group

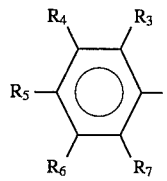

and as (a) the carbon atom bonded to the group

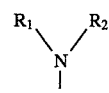

The compounds of formula I contain at least one chiral center, the carbon atom (a).

Moreover, when X is different from

the carbon atom (b) is a chiral center too.

Thus, depending on the meaning of X, the compounds of formula I may exist as two enantiomers or as four stereoisomers two by two enantiomers. It constitutes object of the present invention the use as herbicides of both single enantiomers and racemic or diastereomeric mixture of the compounds of formula I as well as compositions containing them.

Among the meanings of the substituents in formula I, wherever not differently specified, by alkyl we mean a $C_1$–$C_6$, linear or branched alkyl, specific examples being methyl, ethyl, n.propyl, n.butyl, i.butyl, sec.butyl, t.butyl, n.pentyl, i.pentyl, neopentyl, n.hexyl, 2,2-dimethyl-1-butyl.

The alkyl moiety of various substituents like alkoxy, alkylcarbonyl, alkylcarbonyloxy, alkylcarbonylthio, alkoxycarbonyl, alkylthio, alkylsulfinyl, haloalkyl, alkylsulfonyl, mono and dialkylamino, alkylcarbonylamino, is defined as above reported for alkyl. Preferred meanings are $C_1$–$C_4$, alkyls, that is methyl, ethyl, n.propyl, i.propyl, n.butyl, sec.butyl, i.butyl, t.butyl.

Specific and preferred examples of the other groups or substituents present in the compounds of formula I are:

for alkoxycarbonyl: methoxycarbonyl and ethoxycarbonyl;

for alkylcarbonyloxy: acetoxy, propionyloxy;

for alkylcarbonylthio: acetylthio;

for $C_3$–$C_6$ cycloalkyl: cyclopropyl, cyclobutyl, cyclopentyl, cyclohexyl;

for phenylalkyl: benzyl, phenethyl;

for hydroxyiminoalkyl: hydroxyiminomethyl and 1-hydroxyiminoethyl;

for alkoxyiminoalkyl: methoxyiminomethyl;

for alkylthio: methylthio, ethylthio, isopropylthio and the analogs for alkylsulfinyl and alkylsulfonyl;

for heterocycle: furan, thiophene, pyrimidine, 1,3-dithiane, piperidine, morpholine, pyrrole, imidazole, 1,2,4-triazole, tetrazole, oxirane, isoxazole;

for substituted phenyl: 2, 3 or 4-chlorophenyl, 2, 3 or 4-fluorophenyl, 2, 3 or 4-bromophenyl, 2, 3 or 4-tolyl, 2, 3 or 4-ethylphenyl, 2, 3 or 4-methoxyphenyl, 2, 3 or 4-ethoxyphenyl, 2, 3 or 4-nitrophenyl, 2,4-dichlorophenyl, 2-methyl-3-chlorophenyl, 2-chloro-3-methylphenyl, 2,4-dibromophenyl, 2,6-dichlorophenyl, 2,6-dibromophenyl, 2-chloro-6-fluorophenyl, 2,5-dichlorophenyl, 2,6-dimethylphenyl, 2,5-dimethylphenyl, 2,4,6-trimethylphenyl, 2,4-dinitrophenyl, 2-chloro-4-nitrophenyl;

for $C_2$–$C_6$ alkenyl: vinyl, allyl, 2,2-dimethyl-vinyl, 3,3-dimethylallyl;

for $C_2$–$C_6$ alkinyl: propargyl, ethinyl;

for the group

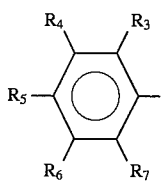

preferred meanings are the same as those above reported for substituted phenyl and also 4-diphenyl ($R_3=R_4=R_6=R_7=H$, $R_5=$phenyl), 4-phenoxy-phenyl, 4-(2-pyridyloxy)-phenyl; preferably at least two of $R_3$, $R_4$, $R_5$, $R_6$ and $R_7$ are hydrogen atoms and preferably at least one of them is different from hydrogen; moreover, other preferred examples are 2, 3 or 4-hydroxyphenyl, 2, 3 or 4-cyanophenyl, 2, 3 or 4-aminophenyl, 2, 3 or 4-dimethylaminophenyl, 2, 3 or 4-diethylaminophenyl 2, 3 or 4-propylaminophenyl, 2, 3 or 4-methylthiophenyl, 2, 3 or 4-ethylthiophenyl, 2, 3 or 4-propylthiophenyl, the analogs sulfinyl or sulfonyl derivatives oxidized at the sulfur atom, 2, 3 or 4-trifluoromethylphenyl, 2, 3 or 4-trichloromethylphenyl, 2-chloro-4-methylthiophenyl, 3-chloro-4-methylthiophenyl, 2-chloro-4-methylsulfonylphenyl, 2-chloro-4-methylsulfonylphenyl; for $R_1$ or $R_2$, when one of $R_1$ and $R_2$ is a hydrogen atom or a $C_1$–$C_3$ alkyl and the other a CO—$R_8$ groups, preferred meanings of CO—$R_8$ are acetyl, formyl, propanoyl, chloroacetyl, bromoacetyl, difluoroacetyl, trifluoroacetyl, dichloroacetyl, trichloroacetyl, hydroxyacetyl, 2,3-dihydroxypropanoyl, dimethylaminoacetyl, acetoxyacetyl, acetacetyl, cyanoacetyl, cyclopropanoyl, cyclobutanoyl, cyclopentanoyl, cyclohexanoyl, hydroxyiminomethylcarbonyl (—CO—CH=N—OH), methoxyiminomethylcarbonyl, 1-hydroxyiminoethylcarbonyl, phenacetyl, methoxyacetyl, methylthioacetyl, methylsulfinylacetyl, methylsulfonylacetyl, methoxycarbonylacetyl, ethoxycarbonylacetyl, isobutyroylacetyl, pivaloyl, 1-tetrazolylacetyl, acryloyl, 3,3-dimethylacryloyl, 2-butenoyl, 3-methyl-2-butenoyl, epoxypropanoyl, 2-chloro-propanoyl, 3-methoxypropanoyl, 3-ethoxypropanoyl, 3-isopropyloxypropanoyl, 1,3-dithiane-2-yl-carbonyl, 2-bromo-3-hydroxy-propanoyl, 3-bromo-2-hydroxy-propanoyl, 2,3-dihydroxy-propanoyl, 2-amino-propanoyl, 2-carbonylaminopropanoyl, 3,3-dichloroacryloyl, aminocarbonyl, methylaminocarbonyl, monoamidosuccinyl, methoxycarbonyl, ethoxycarbonyl, propyloxycarbonyl, isobutyloxycarbonyl, 2,3 or 4-pyridinecarbonyl, 2-furanoyl, 2-thienoyl, 1,3-thiazolyl-2-carbonyl, 3-isoxazolylcarbonyl, 5-isoxazolylcarbonyl; in particular among the meanings of $R_8$ the most preferred are hydrogen, methyl, ethyl, chloromethyl, dichloromethyl, cyanomethyl, methoxymethyl, vinyl, allyl;

among the meanings of $R_9$, the preferred are methyl, ethyl, chloromethyl, phenyl, 4-chlorophenyl, 4-methylphenyl;

among the meanings of $R_{10}$ the preferred are methyl and ethyl;

among the meanings of $R_{11}$ the preferred are hydrogen, methyl and ethyl;

among the meanings of $R_{12}$ the preferred are methyl, ethyl, trifluoromethyl, 1-chloroethyl, cyanomethyl, methoxymethyl, phenyl, 4-methoxy-phenyl;

among the meanings of R specific and preferred meanings are hydrogen, methyl, ethyl, hydroxy, methoxy, ethoxy, fluoro, chloro, bromo, cyano, acetoxy, acetylthio, propanoyloxy;

among the meanings of X, the preferred are:

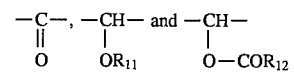

in particular

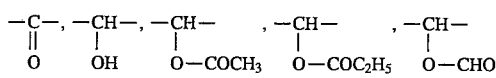

The preferred compounds of formula I are those which possess one of more of the following structural features:

A: at least 2, but at the most 4, of $R_3$, $R_4$, $R_5$, $R_6$ and $R_7$ are hydrogen atoms;

B: one of $R_1$ and $R_2$ is a hydrogen atom or methyl and the other is —CO—$R_8$;

C: X is a group —CO—, —CH(OH), or —CH(OCOCH$_3$)—;

D: R is hydroxy, a fluorine or chlorine atom, methyl or a hydrogen atom.

Inside the compounds which possess the above mentioned structural features, the more preferred compounds are those which possess both features B and D and among these, the still more preferred are those which possess also the structural feature C.

Some of the compounds of formula I are known in the literature. To a restricted number of these, a pharmaceutical activity for human or veterinary use was recognized. Some other compounds of formula I are known as synthetic intermediates. As example we cite the following literature:

British patent No. 770,277 (Parke, Davis & Co.)
British patent No. 745,900 (Sterling Drug Inc.)
French patent No. 1,096,234 (Parke, Davis & Co.)
Cutler et al., J. Am. Chem. Soc., 74, 5475, (1952)
Suter et al., J. Am. Chem. Soc., 75, 4330 (1953)
British patent No. 709,595 (Parke, Davis & Co.)
Rebstock et al., J. Am. Chem. Soc., 77, 186, (1955)
Portelli et al., Ann. Chim., 59, 306, (1969)
Portelli et al., Ann. Chim., 60, 160, (1970)
British patent No. 705,711 (Farmaceutici Italia)
U.S. Pat. No. 2,759,972 (Sterling Drug Inc.)
British patent No. 746,015 (Sterling Drug Inc.)
British patent No. 746,016 (Sterling Drug Inc.)
U.S. Pat. No. 2,816,915 (E. I. Du Pont de Nemours & Co.)
British patent No. 743,446 (Soehne GmbH)
U.S. Pat. No. 2,734,919 (Laboratoires Francais de Chemiotherapie)
British patent No. 699,808 (Parke, Davis & Co.)
Portelli et al., Ann. Chim., 57, 1018, (1967)
U.S. Pat. No. 2,742,500 (E. I. Du Pont de Nemours & Co.)
German patent application No. 2,454,805 (Hoffmann La Roche & Co.)
V. Horak et al., Synthesis, 839, (1984)
European patent No. 14,437 (Schering Corp.)
U.S. Pat. No. 4,743,700 (Zambon S.p.A.)
European patent application No. 130,633 (Zambon S.p.A.)
European patent application No. 323,846 (Nippon Zeon K.K.)
U.S. Pat. No. 4,638,003 (Zambon S.p.A.)
U.S. Pat. No. 4,632,940 (Zambon S.p.A.).

To the best of our knowledge, a herbicidal activity was never recognized to the known compounds of formula I and consequently they have never been indicated as useful in herbicidal compositions for agricultural use.

Always to our knowledge, there are no herbicides commercially used or under development, which have a structure similar to that of the N-alkyl-amides of formula I, therefore, these latters result to be a new class of herbicides.

The preparation of the compounds of formula I is carried out by conventional methods and reactions per se known.

The above cited literature which is herewith incorporated by reference describes various synthetic approaches to the known compounds of formula I as well as the preparation or separation of the different stereoisomers.

The preparation of the new compounds of formula I is carried out by fitting the literature techniques in a per se conventional way.

Particularly useful intermediates for the synthesis of the compounds of formula I, are the compounds of formula

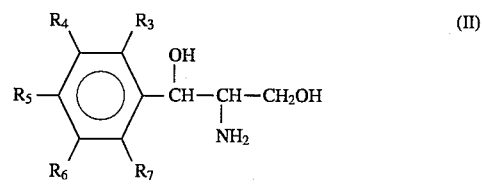

wherein $R_3$, $R_4$, $R_5$, $R_6$ and $R_7$ have the above reported meanings.

The aminodiols of formula II can be prepared accordance to different procedures reported in the literature which in general refer to the preparation of micamine [II, ($R_3=R_4=R_6=R_{7=H}$, $R_5=NO_2$) an intermediate for the preparation of the antibiotic Chloramphenicol (Merck Index, 10th Ed., No. 2035, page 289] or of thiomicamine (II, $R_3=R_4=R_6=R_7=H$, $R_5=CH_3S$) an intermediate for the preparation of the antibiotic Thiamphenicol (Merck Index, 10th Ed., No. 9140, page 1332).

By fitting the process described in British patent No. 746,015 or by R. A. Cutler et al., J. Am. Chem. Sot., 74, 5475, (1952) and the references cited therein, an acetophenone of formula

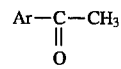

wherein Ar represent the group

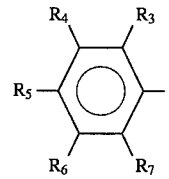

is transformed into the corresponding bromoacetophenone by reaction with bromine in chloroform

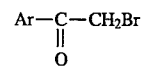

and this is made to react with hexamethylenetetramine to afford an intermediate of formula

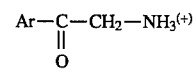

which is N-protected as N-acyl-derivative and made to react with formaldehyde in the presence of a base thus affording the compounds of formula

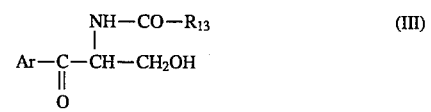

(wherein CO—$R_{13}$ is an acyl radical and $R_{13}$ can have the same meanings of $R_8$).

The reduction of compound III, e.g. by aluminum isopropoxide, affords a compound of formula

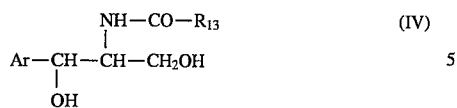 (IV)

The optional deprotection of the nitrogen atom affords the compounds of formula II.

According to an alternative procedure, by fitting the method described in U.S. Pat. No. 2,816,915, an aldehyde of formula

is condensed with glycine to afford an intermediate of formula

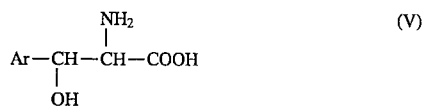 (V)

The esterification of compound V affords a compound of formula

 (VI)

wherein $R_{14}$ is an alkyl.

The reduction of compound VI affords compound II.

Obviously, when $R_{13}$ has the same meanings as $R_8$, the compounds of formula III and IV ape already herbicide compounds of formula I.

Compounds of formula III: formula I wherein

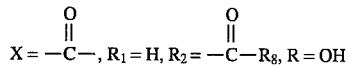

Compounds of formula IV: formula I wherein X=—CH(OH)—, $R_1$=H,

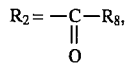

R=OH

Depending on the meanings of $R^3$, $R^4$, $R_5$, $R_6$ and $R_7$, the corresponding compounds of formula II are prepared according to one of the above described procedures.

The two procedures are useful also for preparing single stereoisomers or diastereomeric or enantiomeric mixtures of the compounds of formula II.

In any case, alternative procedures are known for the stereoselective synthesis or for stereoisomers separation of some of the compounds of formula II which may be fitted for the preparation of the others.

For example

Ann. Chim., 59, 306, (1969)

U.S. Pat. No. 2,767,213

British patent No. 705,711

J. Am. Chem. Soc., 77, 186, (1955)

wherein enantiomers separations are described by resolution according to the formation of salts with optically active acids. This literature is herewith incorporated by reference too.

From the compounds of formula II the other compounds of formula I are readily prepared by per se known reactions.

For example, the oxidation of the benzylic hydroxy affords the compounds of formula I wherein X=—CO—.

The oxidation may be carried out according to what reported by V. Horak et al., Synthesis, 839, (1984).

The acylation of the benzylic hydroxy of the compounds of formula II by an acyl-halogenide in the presence of a base affords the intermediates for the compounds of formula I wherein X=—CH(OCOR$_{12}$)—.

The transformation of the benzylic hydroxy of the compounds of formula II into an ester affords also the intermediates for the compounds of formula I wherein X=—CH(OR$_{11}$) and R$_{11}$ is different from hydrogen or alkyl.

The substitution of the benzylic hydroxy of the compounds of formula II by known methods affords the intermediates for the compounds of formula I wherein X=—CH(Cl)—, —CH(Br)—, —CH(F)—.

The N-acylation of a compound of formula II or of another intermediate in which X has different meanings, affords the compounds of formula I wherein one of $R_1$ and $R_2$ is a hydrogen atom and the other a COR$_8$ group. The same compounds may also be prepared by the above described methods (Compounds of formula III and IV).

The acylation of the primary hydroxy in the compounds of formula II e.g. by an acyl-halide in the presence of a tertiary amine, affords the compounds of formula I wherein R is an alkylcarbonyloxy group.

The nucleophilic substitution of the primary hydroxy groups of the suitably protected compounds of formula II, optionally activated as mesyl or tosyl derivative, affords the compounds of formula I wherein R=Cl, Br.

Suitable reagents are thionyl chloride or CBr$_4$ in the presence of triphenylphosphine respectively.

The compounds of formula I wherein R=CN can be prepared starting from those in which R=Cl, Br by treatment with an alkaline cyanide.

Alternatively, said compounds can be prepared starting from compounds of formula

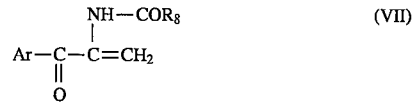 (VII)

by reaction with sodium cyanide.

The compounds of formula VII are useful also for the preparation of the compounds of formula I wherein R=alkylcarbonylthio by reaction with the corresponding thiocarboxylic acids, and optionally from these by hydrolysis, the compounds wherein R=SH are obtained.

The compounds of formula VII are prepared starting from the compounds of formula II which are acylated or the nitrogen atom and on the primary hydroxy group (e.g. by acetyl chloride) and oxidized to ketone, then by treatment with a base, they give an elimination reaction thus affording the unsaturated compounds of formula VII.

The compounds of formula I wherein R is a fluorine atom can be prepared by substitution of the primary hydroxy group with fluorine according to the procedures described in the European patent No. 14,437 or in the U.S. Pat. No. 4,743,700.

Finally, it must be pointed out that also the groups present on the aromatic ring ($R_3$, $R_4$, $R_5$, $R_6$ and $R_7$) can be modified by per se known reactions like reduction of a nitro group to amino, acylation of this latter, diazotization and replacement of the amino by halogen, oxidation of an alkylthio group to alkylsulfinyl or alkylsulfonyl, and the alkylation of phenolic hydroxy.

It is clear to the expert in the field that in order to carry out all the above cited reactions, it may be necessary to protect the functions already present in the molecule, in particular it may be necessary to protect one or both the hydroxy groups and the amino groups. The protection and the subsequent deprotection are carried out according to known methods.

For a compendium of the said known methods reference is made to T. W. Greene, "Protective Groups in Organic Synthesis", J. Wiley & Son, New York.

In an analogous way, the protection can also be carried out by the formation of cyclic intermediates like, e.g., the 1,3-oxazolidines described in the European patent application No. 130,633 (Zambon S.p.A.) and in Tetrahedron, 29, (1988), 5561.

The above reported reactions are per se known and can be realized as such or by fitting the known techniques. The order according to which the various transformations must be carried out, starting for example from the compounds of formula II, depends on the specific groups that it is desired to introduce and the selection of the synthetic strategy is within the normal knowledge of the expert in the field.

Moreover, the compounds of formula I themselves, having various functional groups, can be useful as starting products for the preparation of other compounds of formula I according to well-known chemical transformations.

Obviously, the synthesis of specific compounds of formula I may require a synthetic strategy different from those above described.

In any case, the cited literature and the examples in the following give a sufficient guidance that the chemist expert in the field can integrate with his normal knowledge.

The following table 1 reports some specific examples of compounds of formula I prepared according to the above described methods.

The synthesis of some meaningful compounds is reported in the examples.

TABLE 1

Compounds of formula

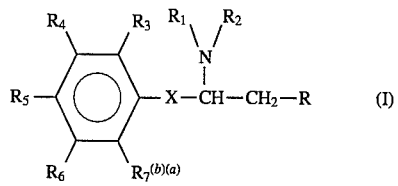

(I)

| Compound No. | X | R | $R_1$ | $R_2$ | (a) $R_3$–$R_7$ | (b) Configuration | (c) M.p. (°C.) |
|---|---|---|---|---|---|---|---|
| 1 | CH(OH) | F | H | CO—CH=CH$_2$ | 4-CH$_3$SO$_2$ | S,R | 180–181 |
| 2 | CH(OH) | F | H | CO—C(CH$_3$)=CH$_2$ | 4-CH$_3$SO$_2$ | S,R | 121–123 |
| 3 | CH(OH) | F | H | CO—cyclopropyl | 4-CH$_3$SO$_2$ | S,R | 164–166 |
| 4 | CH(OH) | F | H | CO—CH$_2$—OCH$_3$ | 4-CH$_3$SO$_2$ | S,R | 177–179 |
| 5 | CH(OH) | F | N | CO—CH=C(CH$_3$)$_2$ | 4-CH$_3$SO$_2$ | S,R | 143–144 |
| 6 | CH(OH) | F | H | CO—CH=CH—CH$_3$ | 4-CH$_3$SO$_2$ | S,R | 161–163 |
| 7 | CH(OH) | F | H | CO—furyl | 4-CH$_3$SO$_2$ | S,R | 163–165 |
| 8 | CH(OH) | F | H | CO—CH$_2$Cl | 4-CH$_3$SO$_2$ | S,R | 154–156 |
| 9 | CH(OH) | F | H | CO—CH(CH$_3$)$_2$ | 4-CH$_3$SO$_2$ | S,R | 155–157 |
| 10 | CH(OH) | F | H | CO—CH(Cl)—CH$_3$ | 4-CH$_3$SO$_2$ | S,R | 134–136 |
| 11 | CH(OH) | F | H | CO—CH$_3$ | 4-CH$_3$SO$_2$ | S,R | 131–133 |
| 12 | CH(OH) | F | H | CO—CH$_2$—CH$_3$ | 4-CH$_3$SO$_2$ | S,R | 134–136 |
| 13 | CH(OH) | F | H | CO—C(CH$_3$)$_3$ | 4-CH$_3$SO$_2$ | S,R | 168–170 |
| 14 | CH(OH) | F | H | CO(CH$_2$)$_2$OCH(CH$_3$)$_2$ | 4-CH$_3$SO$_2$ | S,R | 83–85 |
| 15 | CH(OH) | F | H | COOCH$_2$CH(CH$_3$)$_2$ | 4-CH$_3$SO$_2$ | S,R | 124–126 |
| 16 | CH(OH) | F | H | COOEt | 4-CH$_3$SO$_2$ | S,R | 98–99 |
| 17 | CH(OH) | F | H | COCH$_2$OCOCH$_3$ | 4-CH$_3$SO$_2$ | S,R | 113–115 |
| 18 | CH(ON) | F | H | CO—CH$_2$—CN | 4-CH$_3$SO$_2$ | S,R | 152–154 |
| 19 | CH(OH) | F | H | COCH$_2$COOEt | 4-CH$_3$SO$_2$ | S,R | 156–158 |
| 20 | CH(OH) | F | H | CO—C(CH$_3$)$_2$—CN | 4-CH$_3$SO$_2$ | S,R | 119–121 |
| 21 | CH(OH) | F | H | CO—CH$_2$—CN | 4-CH$_3$SO$_2$ | R,S | 152–154 |
| 22 | CH(OH) | OH | H | CO—CH$_2$—CN | 4-CH$_3$SO$_2$ | R,R | 152–154 |
| 23 | CH(OH) | OH | H | CO—CH$_2$—CN | 4-CH$_3$SO$_2$ | S,S | 154–156 |
| 24 | CH(OH) | OH | H | CO—CH$_2$—CN | 4-CH$_3$S | S,S | 134–136 |
| 25 | CH(OH) | OH | H | CO—CH—Cl$_2$ | 4-CH$_3$S | S,S | 110–112 |
| 26 | —CH(OH)— | F | H | CO—CF$_3$ | 4-CH$_3$SO$_2$ | S,R | 146–148 |
| 27 | —CH(OH)— | OH | H | CO—CH—Cl$_2$ | 4-CH$_3$SO$_2$ | R,R | 166–168 |
| 28 | CH(OH) | H | H | CO—CH$_2$—CN | 4-CH$_3$S | RS,RS | 116–118 |
| 29 | CH(OH) | CH$_3$ | H | CO—CH$_2$—CN | 4-CH$_3$S | RS,RS | 190–192 |
| 30 | CH(OH) | H | H | CO—CH$_2$—CN | 4-Br | RS,RS | 123–125 |
| 31 | CH(OH) | H | H | CO—CH$_2$—CN | 3CF | RS,RS | 78–80 |
| 32 | CH(OH) | OH | H | CO—CH$_2$—CN | 3CF$_3$ | RS,RS | (d) |

TABLE 1-continued

Compounds of formula $$\begin{array}{c} R_4 \quad R_3 \quad R_1 \diagdown R_2 \\ | \quad | \quad N \\ R_5 - \text{[phenyl ring]} - X - CH - CH_2 - R \quad (I) \\ | \quad | \\ R_6 \quad R_7^{(b)(a)} \end{array}$$

| Compound No. | X | R | R₁ | R₂ | (a) R₃–R₇ | (b) Configuration | (c) M.p. (°C.) |
|---|---|---|---|---|---|---|---|
| 33 | CH(OH) | OH | H | CO—CH—Cl₂ | 4-CH₃S | R,R | 111.5–112.5 |
| 34 | CH(OH) | F | H | CO—CH—Cl₂ | 4-CH₃SO₂ | S,R | 152–154 |
| 35 | CH(OCOH) | F | H | COH | 4-CH₃SO₂ | S,R | 126–128 |
| 36 | CH(OH) | F | H | CO—CH₂—SCH₃ | 4-CH₃SO₂ | S,R | 144–146 |
| 37 | CH(OH) | F | H | CO—(dithiolane) | 4-CH₃SO₂ | S,R | 132–134 |
| 38 | CH(OH) | F | H | CO—CH=N—OCH₃ | 4-CH₃SO₂ | S,R | 159–161 |
| 39 | CH(OH) | F | H | CO—CH(OC₂H₅)₂ | 4-CH₃SO₂ | S,R | 87–89 |
| 40 | CH(OH) | F | H | CHO | 4-CH₃SO₂ | S,R | 134–135 |
| 41 | CH(OH) | F | H | COC≡CH | 4-CH₃SO₂ | S,R | 148–150 |
| 42 | CH(OH) | F | H | CO—CH₂—CO—CH₃ | 4-CH₃SO₂ | S,R | 139–141 |
| 43 | CH(OH) | F | H | CONH₂ | 4-CH₃SO₂ | S,R | 201–203 (e) |
| 44 | CH(OH) | F | H | SO₂—C₆H₅ | 4-CH₃SO₂ | S,R | 184.5–186.5 |
| 45 | CH(OH) | F | H | SO₂CH₃ | 4-CH₃SO₂ | S,R | 136–138 |
| 46 | CH(OH) | F | H | SO₂C₂H₅ | 4-CH₃SO₂ | S,R | 150–152 |
| 47 | CH(OH) | F | H | SO₂CH₂Cl | 4-CH₃SO₂ | S,R | 154–156 |
| 48 | CH(OH) | F | H | PO(OCH₃)₂ | 4-CH₃SO₂ | S,R | 153–155 (e) |
| 49 | CH(OH) | F | H | COCH=N—OH | 4-CH₃SO₂ | S,R | 143–145 |
| 50 | CH(OH) | F | H | CO—C(CH₃)=N—OH | 4-CH₃SO₂ | S,R | 180–182 |
| 51 | CH(OH) | F | H | CO—CH₂—C(CH₃)=N—OCH₃ | 4-CH₃SO₂ | S,R | 107–109 |
| 52 | CH(OH) | F | H | CO—C(CH₃)=N—OCH₃ | 4-CH₃SO₂ | S,R | 139–141 |
| 53 | CH(OH) | F | H | COCH₂—N(tetrazole) | 4-CH₃SO₂ | S,R | (d) |
| 54 | CH(OH) | F | H | CO—CH₂—N₃ | 4-CH₃SO₂ | S,R | 119–121 |
| 55 | CH(OH) | F | H | CO—CO—NH₂ | 4-CH₃SO₂ | S,R | 208–210 |
| 56 | CH(OH) | F | H | COCOOH | 4-CH₃SO₂ | S,R | 160–162 (e) |
| 57 | CH(OH) | F | H | CO—CH₂—OH | 4-CH₃SO₂ | S,R | 160–162 |
| 58 | CH(OH) | F | H | CO—CH₂—SO—CH₃ | 4-CH₃SO₂ | S,R | 135–137 |
| 59 | CH(OH) | F | H | CO—CH₂—SO₂—CH₃ | 4-CH₃SO₂ | S,R | 167–169 |
| 60 | CH(OH) | F | H | CO—CH(OH)—CH₂—Br | 4-CH₃SO₂ | S,R | 142–144 |
| 61 | CH(OH) | F | H | CO—CH(Br)—CH₂—OH | 4-CH₃SO₂ | S,R | 114–116 |
| 62 | CH(OH) | F | H | CO—(oxirane) | 4-CH₃SO₂ | S,R | 132–134 |
| 63 | CH(OH) | F | H | CO—CH(OH)—CH₂—OH | 4-CH₃SO₂ | S,R | 160–162 |
| 64 | CH(OH) | F | H | CO—CH(NH₂)—CH₃ | 4-CH₃SO₂ | S,R | 132–134 |
| 65 | CH(OH) | OH | H | COOC₂H₅ | 4-CH₃S | R,R | 73–75 |
| 66 | CH(OH) | OH | H | CO—CH₂—Cl | 4-CH₃S | R,R | 73–75 |
| 67 | CH(OH) | OH | H | CO—CH₂—Cl | 4-CH₃S | S,S | 73–75 |
| 68 | CH(ONO₂) | F | H | CO—CH—Cl₂ | 4-CH₃SO₂ | S,R | (d) |
| 69 | C=O | F | H | CO—CH—Cl₂ | 4-CH₃SO₂ | S | 161–163 |
| 70 | C=O | OH | H | CO—CH—Cl₂ | 4-CH₃SO₂ | R | 172–174 |
| 71 | CH(OCOCH₃) | F | H | CO—CH=CH₂ | 4-CH₃SO₂ | S,R | (d) |
| 72 | CH(OH) | OCH₃ | H | CO—CH₂—CN | 4-CH₃SO₂ | R,R | 152 |
| 73 | CH(OCH₃) | OH | H | CO—CH₂—CN | 4-CH₃SO₂ | R,R | 125 |
| 74 | CH(OH) | CH₃ | H | CO—CH₂—CN | 4-CH₃SO | RS,RS | (d) |
| 75 | CH(OH) | OH | H | CO—CH—Cl₂ | 4-CH₃SO | R,R | 34–36 |
| 76 | CH(OH) | OH | H | CO—CH₂—Cl | 4-CH₃SO₂ | R,R | 136–138 |
| 77 | CH(OH) | OH | H | CO—CH₂—Cl | 4-CH₃SO₂ | S,S | 136–138 |
| 78 | CH(OH) | CH₃ | H | CO—CH₂—CN | 4-CH₃SO₂ | RS,RS | 165–167 |
| 79 | CH(OH) | OCOCH₃ | H | COCH₃ | 4-CH₃SO₂ | S,S | 131–133 |
| 80 | CH(OH) | OCOCH₃ | H | CO—CH—Cl₂ | 4-CH₃S | S,S | 100–101 |
| 81 | CH(OCOCH₃) | F | H | COH | 4-CH₃SO₂ | S,R | (d) |

TABLE 1-continued

Compounds of formula $$R_5 - \underset{R_6}{\underset{|}{C_6H_3}}(R_4)(R_3)(R_7) - X - CH(NR_1R_2) - CH_2 - R \quad (I)$$

| Compound No. | X | R | $R_1$ | $R_2$ | (a) $R_3-R_7$ | (b) Configuration | (c) M.p. (°C.) |
|---|---|---|---|---|---|---|---|
| 82 | CH(OH) | OCOCH$_3$ | H | CO—CH$_2$—CN | 4-CH$_3$S | S,S | 138–140 |
| 83 | CH(OH) | OCOCH$_3$ | H | CO—CH$_2$—Cl | 4-CH$_3$S | S,S | 94–96 |
| 84 | CH(OH) | OCOCH$_3$ | H | CO—CH—Cl$_2$ | 4-CH$_3$SO$_2$ | R,R | 140–142 |
| 85 | CH(OCOCH$_3$) | OCOCH$_3$ | H | CO—CH—Cl$_2$ | 4-CH$_3$SO$_2$ | R,R | 120–122 |
| 86 | CH(OCOC$_6$H$_5$) | F | H | CO—CH—Cl$_2$ | 4-CH$_3$SO$_2$ | S,R | 129–131 |
| 87 | CH(OCOCH$_3$) | F | H | CO—CH$_2$—CN | 4-CH$_3$SO$_2$ | S,R | (d) |
| 88 | CH(OCOCH$_3$) | F | H | CO—CH$_2$—CN | 4-CH$_3$SO$_2$ | R,S | (d) |
| 89 | C=O | OCOCH$_3$ | H | CO—CH$_2$—Cl | 4-CH$_3$S | S | 136–138 |
| 90 | C=O | OCOCH$_3$ | H | COCH$_3$ | 4-CH$_3$S | S | 141–143 |
| 91 | C=O | OCOCH$_3$ | H | CO—CH—Cl$_2$ | 4-CH$_3$S | S | 124–126 |
| 92 | C=O | OCOCH$_3$ | H | COCH$_3$ | 4-CH$_3$SO$_2$ | S | 129–131 |
| 93 | CH(OH) | H | H | CO—CH$_2$—CN | 4-CH$_3$SO$_2$ | R,R e S,S | 190–191 |
| 94 | CH(OH) | H | H | CO—CH$_2$—CN | 4-CH$_3$SO$_2$ | R,S e S,R | 130–132 |
| 95 | C=O | CN | H | COCH$_3$ | 4-CH$_3$S | RS | 153–155 |
| 96 | C=O | SCOCH$_3$ | H | COCH$_3$ | 4-CH$_3$S | RS | 121–123 |
| 97 | C=O | H | H | COCH$_3$ | 4-CH$_3$SO$_2$ | RS | 143–145 |
| 98 | C=O | H | H | CO—CH—Cl$_2$ | 4-CH$_3$SO$_2$ | RS | 144–146 |
| 99 | CH(OH) | F | H | COCOOC$_2$H$_5$ | 4-CH$_3$SO$_2$ | S,R | (d) |
| 100 | CH(OH) | F | H | COCOCH$_3$ | 4-CH$_3$SO$_2$ | S,R | (d) |
| 101 | CH(OH) | F | H | CO—CH(CH$_3$)—NH—COH | 4-CH$_3$SO$_2$ | S,R | 139–141 |

Notes to Table 1
(a) Substituents from $R_3$ to $R_7$ not reported in the table are hydrogen.
(b) The configuration of the chiral centres a and b are reported in said order. When a is not a chiral centre, the reported configuration refers to the b centre.
(c) The $^1$H-NMR spectra of all the compounds of table 1 are consistent with the assigned structure.
(d) The $^1$H-NMR spectrum is reported in the relevant example.
(e) Decomposition on melting.

The compounds of formula I are endowed with herbicidal activity which is displayed both in the pre-emergence and in the post-emergence treatments, both with respect to monocotyledons and dicotyledons.

The compounds of formula I, moreover, administered in very low doses have shown a certain activity as phytoregulators.

The herbicidal activity was evidenced by laboratory tests in which the weeds, both monocotyledons and dicotyledons, were directly treated or in which the soil wherein weeds were seeded was treated. The procedure is described in detail in example 43.

Within the class consisting of the compounds of formula I specific compounds are more effective in the pre-mergence treatment, others in the post-emergence treatment.

Better results are obtained in the post emergence treatment and against dicotyledons, even though a number of compounds are remarkably active in the pre-emergence treatment and against monocotyledons.

For these reasons it can be useful, under certain treatment conditions, to combine two or more of the compounds of formula I having complementary herbicidal characteristics.

Up to now, the preferred compounds of formula I are those in which one of $R_1$ and $R_2$ is hydrogen and the other is a CO—$R_8$ group.

Within said group, the most interesting compounds are those in which $R_8$ is hydrogen or a substituted alkyl.

In the practical agricultural applications the compounds of formula I will be distributed in doses comprised between 0.03 and 6 kg/ha depending on various factors among which the followings may be cited:

treatment in pre- or post-emergence the kind of weeds, present or expected, and the degree of infestation, real or foreseen the type of composition used climatic or environmental factors the relative efficacy of the used compound or compounds of formula I also as a function of the other above listed factors.

Preferably the dose to be used is comprised between 0.05 and 2 kg/ha.

The herbicide compositions object of the invention comprise one or more of the compounds of formula I as active ingredient and a carrier beside optional additives of agricultural use.

The carrier can be solid (e.g. bentonite, kaolin, hydrated calcium sulfate or their mixtures) or liquid (e.g. organic solvents, water or their mixtures) and the composition can have the form of dry powder, wettable powder, granulate, solution, suspension, emulsifiable concentrate or flowable.

The additives optionally present depend on the type of composition and can be selected among, e.g. wetting agents, adhesives, suspending agents, solubilizing agents, surfactants and dyes.

When useful with respect to the treatment of specific infestation conditions, it is possible to add to the compositions other biologically active compounds useful in agriculture such as fertilizers, fungicides or other herbicides.

The preparation of the compositions of the invention is carried out according to conventional techniques.

The following example are now given with the aim to better illustrate the invention without limiting it.

EXAMPLE 1

Preparation of N-[(1S,2R)-1-fluoromethyl-2-hydroxy-2-(4-methylsulfonylphenyl)ethyl]-2-propenamide (Compound 1)

A mixture of acryloyl chloride (33.18 g; 0.366 mol) in methylene chloride (336 ml) and 1N sodium hydroxide (366 ml) were contemporaneously added dropwise, by keeping the pH value at about 9 and the temperature lower than +5° C., into a mixture of (1R,2S)-2-amino-3-fluoro-1-(4-methylsulfonylphenyl)-1-propanol hydrochloride (80 g; 0.282 mol) in methylene chloride (2050 ml) and 1N sodium hydroxide (282 ml), cooled to 0° C.

At the end of the addition the reaction mixture was kept under stirring for 30 minutes at 0° C. and then for 1 hour at room temperature, by controlling the pH and by adding further 1N sodium hydroxide if necessary.

Tetrahydrofuran (2500 ml) was then added and the phases were separated. The aqueous phase was again extracted with tetrahydrofuran and then the combined organic layers were washed in sequence with water, 5% HCl, water, aqueous sodium bicarbonate and at last again with water.

After drying and evaporation under vacuum the crude crystalline product (61.6 g) was treated with tert.butylmethylether.

The crude was then purified by crystallization with a mixture of acetonitrile/tert.butylmethylether=4:1.

Compound 1 was obtained (56 g; 65.9% yield) with m.p. 180°–181° C.

By the same method the compounds from 2 to 17 reported in Table 1 were prepared.

EXAMPLE 2

Preparation of (1RS,2RS)-2-amino-1-(4-methylthiophenyl)-1-butanol (Intermediate 1)

4-Methylthiobenzaldehyde (15.2 g), 1-nitropropane (20.5 g) and ethanol (80 ml) were charged in a 250 ml two-necked flask, equipped with thermometer, dropping funnel and magnetic stirrer.

It was cooled to 5° C. and a sodium hydroxide solution (4.2 g) in water (40 ml) was added under vigorous stirring.

The reaction mixture was stirred at room temperature overnight.

At the end of the reaction it was neutralized with 2% acetic acid and was kept at the temperature of 4° C. overnight. The precipitate was filtered off and the filtrate was extracted with methylene chloride. The organic solvent was evaporated to give as a whole 22.6 g of a crude product.

The crude was then chromatographed on silica gel, eluent methylene chloride, to give 2-nitro-1-(4-methylthiophenyl)-1-butanol (7.6 g) 2-Nitro-1-(4-methylthiophenyl)-1-butanol (7.5 g), zinc powder (9.2 g) and ethanol (15.5 ml) were introduced in a 250 ml three-necked flask, equipped with reflux condenser, thermometer, dropping funnel and magnetic stirrer. A solution formed by 96% sulfuric acid (6.7 ml) and water (40 ml) was then added dropwise at a temperature between 30° and 40° C. It was stirred overnight at room temperature.

At the end of the reaction the unreacted zinc was filtered off and the filtrate was washed with ethyl ether.

The aqueous phase was made basic with 50% sodium hydroxide and extracted with ethyl ether.

The organic phase was dried over sodium sulfate and the solvent was evaporated under reduced pressure.

The obtained crude product was chromatographed on silica gel, eluent methylene chloride/methanol=94:6, to give intermediate 1 (4.2 g).

A portion of the obtained product dissolved in ethyl ether was treated with ethereal hydrochloric acid to give the hydrochloride with m.p. 113°–115° C.

By an analogous way the following compounds, as threo and erythro mixtures, were prepared:

2-amino-1-(4-methylthiophenyl)-1-propanol (Intermediate 2)—m.p. (hydrochloride) 188° C.

2-Amino-1-(4-bromophenyl)-1-propanol (Intermediate 3)—m.p. (hydrochloride) 223°–225° C.

2-Amino-1-(3-trifluoromethylphenyl)-1-propanol (Intermediate 4)—m.p. (hydrochloride) 155°–157° C.

2-Amino-1-(3-trifluoromethyl)-1,3-propanediol (Intermediate 5)

NMR (acetone $D_6$): δ (ppm): 3.0–3.3 (m, 1H, —CH—N); 3.5–3.9 (m, 2H, $CH_2$—O); 4.1 (bs, 4H, 2OH, $NH_2$); 4.7–5.3 (m, 1H, CH—O); 7.3–7.8 (m, 4H, aromatics).

EXAMPLE 3

Preparation of 2-cyano-N-[(1S,2R)-1-fluoromethyl-2-hydroxy-2-(4-methylsulfonylphenyl)ethyl]-acetamide (Compound 18)

A mixture of (1R,2S )-2-amino-3-fluoro-1-(4-methylsulfonylphenyl)-1-propanol hydrochloride (5.66 g; 20 mmol), absolute ethanol (27 ml), ethyl cyanoacetate (22.62 g; 200 mmol) and triethylamine (3.03 g; 30 mmol) was refluxed for 21 hours.

The solution was then evaporated to reduced volume and the residue was collected with tetrahydrofuran and washed with a sodium chloride saturated solution to neutral pH.

After drying and evaporation of the organic phase a crude crystalline product was obtained which was purified by crystallization from absolute ethanol twice. Compound 18 (3.2 g; 50.9%) was obtained with m.p. 152°–154° C.

By the same method the compounds from 19 to 34 and 99, reported in Table 1, were prepared.

EXAMPLE 4

Preparation of (1R,2S)-3-fluoro-2-formamido-1-(4-methylsulfonylphenyl)-propyl formiate (Compound 35)

Acetic anhydride (7.2 ml) was added dropwise in 20 minutes to a mixture of (1R,2S)-2-amino-3-fluoro-1-(4-methylsulfonylphenyl)-1-propanol (2.47 g; 10 mmol) in formic acid (20 ml), heated to 48° C. After 4 hours the heating was interrupted and after 3 days water (100 ml) was added and the mixture was evaporated under vacuum. The residue was collected with dichloromethane and washed with water, diluted hydrochloric acid and water at neutral pH. The organic phase was dried and evaporated to give a thick oil (2 g) which slowly crystallized and was then treated with ethyl acetate.

Compound 35 (0.8 g; 26% yield) was obtained with m.p. 126°–128° C.

A portion of this product was treated for 1 hour at room temperature with an equimolecular amount of 1N sodium hydroxide. Compound 40 reported in Table 1 was obtained (m.p. 134°–135° C.).

EXAMPLE 5

Preparation of
N-[(1S,2R)-1-fluoromethyl-2-hydroxy-2-
(4-methylsulfonylphenyl)ethyl]-2-methylthioacetamide
(Compound 36)

A solution of dicyclohexylcarbodiimide (2.6 g; 10 mmol) in acetonitrile (20 ml) was added dropwise to a mixture of 2-methylthioacetic acid (1.06 g; 10 mmol) and N-hydroxysuccinimide (1.208g; 10.5 mmol) in acetonitrile (15 ml) cooled to 0° C.

After one night the suspension was filtered off and the filtrate was evaporated under vacuum; an oily residue of reactive ester (2.02 g) was obtained which was used as such.

A suspension of (1R,2S)-2-amino-3-fluoro-1-(4-methylsulfonylphenyl)-1-propanol hydrochloride (2.838 g; 10 mmol) and triethylamine (2.80 ml; 20 mmol) in acetonitrile (30 ml) was prepared, cooled to 0° C. and the reactive ester, as above prepared, dissolved in acetonitrile (30 ml) was added dropwise.

After one night at room temperature it was concentrated under vacuum and the residue was collected with tetrahydrofuran and washed first with acidic brine, then with basic sodium bicarbonate brine, and finally with neutral brine. The solution was dried and evaporated under vacuum. The residue was crystallized from acetonitrile.

Compound 36 (2 g; 59.6% yield) was obtained with m.p. 144°–146° C.

By the same method the of 37, 38 and 100 reported in Table 1 were prepared.

NMR of compound 100:

$^1$H-NMR (DMSO-$d_6$) (60 MHz): δ (ppm): 2.3 (s, 3H, $CH_3CO$); 3.2 (s, 3H, $CH_3SO_2$); 4.0–5.2 (m, 4H, CH—CH—$CH_2$); 6.1 (d, 1H, OH); 7.5–8.1 (m, 4H, aromatics); 8.2 (d, 1H, NH).

EXAMPLE 6

Preparation of
2,2-diethoxy-N-[(1S,2R)-1-fluoromethyl-
2-hydroxy-2-(4-methylsulfonylphenyl)ethyl]-acetamide
(Compound 39)

A mixture of ethyl diethoxyacetate (5.4 ml; 30 mmol) and triethylamine (8.4 ml; 120 mmol) in water (30 ml) and ethanol (10 ml) was heated to reflux for 17 hours. At the end of the heating the solvent and the base in excess were evaporated and the oily residue was dissolved in methylene chloride (40 ml). A mixture of isobutylchloroformate (4.1 g; 30 mmol) in methylene chloride (15 ml) was cooled to −12° C. and added dropwise in a few minutes.

After 15 minutes at −5° C., a solution of (1R,2S)-2-amino-3-fluoro-1-(4-methylsulfonylphenyl)-1-propanol hydrochloride (8.51 g; 30 mmol) in methylene chloride (100 ml) and triethylamine (3.03 g; 30 mmol) was added dropwise.

After 30 minutes at −5° C. the temperature was left to rise to 25° C. and after 2 hours the mixture was treated with water, the organic phase was separated and washed with 5% HCl and then with water up to neutrality.

The residue obtained by evaporation of the solvent was dried and purified by silica gel chromatography, eluent ethyl acetate/dichloromethane=1:1. The product was recrystallized by tert.butylmethylether to give compound 39 (5 g; 44.2% yield) with m.p. 87°–89° C.

From the same preparation, during the chromatography, the compound 15 (1 g) reported in Table 1 (see also example 1) was isolated as product with major Rf.

EXAMPLE 7

Preparation of
N-[(1S,2R)-1-fluoromethyl-2-hydroxy-2-
(4-methylsulfonylophenyl)ethyl]-propiolamide
(Compound 41)

Sodium hydride (80% in vaseline) (0.6 g; 20 mmol) was added portion-wise by keeping the temperature at 0° C. to a solution of propiolic acid (1.40 g; 20 mmol) in tetrahydrofuran (20 ml). The reaction was completed by heating up to 50° C. for 5 hours and then was cooled again to 0° C. and oxalyl chloride (1.27 g; 10 mmol) was added.

After 1 hour at room temperature the mixture was cooled to +10° C. and a solution of (1R,2S)-2-amino-3-fluoro-1-(4-methylsulfonylphenyl)-1-propanol (2.47 g; 10 mmol) and triethylamine (1.39 ml; 10 mmol) in acetonitrile (25 ml) was added dropwise.

After 2 hours the solvents were evaporated under vacuum and the residue was collected with tetrahydrofuran. The dark solution was washed with acidic and then neutral brine. The residue which was obtained by evaporation of the solvent was purified by silica gel chromatography by eluting with dichloromethane/methanol=9:1.

Crystalline compound 41 (0.65 g; 21.7% yield) was obtained with m.p. 148°–150° C.

EXAMPLE 8

Preparation of
N-[(1S,2R)-1-fluoromethyl-2-hydroxy-2-
(4-methylsulfonylphenyl)ethyl]-3-oxo-butanamide
(Compound 42)

Diketene (1.682 g; 20 mmol) dissolved in methylene chloride (4 ml) was added dropwise, at room temperature, to a mixture of (1R,2S)-2-amino-3-fluoro-1-(4-methylsulfonylphenyl)-1-propanol hydrochloride (5.66 g; 20 mmol) and triethylamine (2.024 g; 20 mmol) in methylene chloride.

After 3 hours 3% hydrochloric acid was added and the phases were separated, the aqueous phase was salted with sodium chloride and extracted with tetrahydrofuran. The organic layers were dried and evaporated to give a crystalline residue (5.2 g) which after recrystallization from 1,2-dichloroethane gave the compound 42 (4.2 g) with m.p. 139°–141° C.

EXAMPLE 9

Preparation of N-[(1S,
2R)-1-fluoromethyl-2-hydroxy-2-
(4-methylsulfonylphenyl)ethyl]-urea (Compound
43)

Sodium cyanate (1.3 g; 20 mmol) dissolved in water (11 ml) was added dropwise, by keeping the temperature between 35° and 40° C., to a solution of (1R,2S)-2-amino- 3-fluoro-1-(4-methylsulfonylphenyl)-1-propanol (2.47 g; 10 mmol) in acetic acid (4.8 ml) and water (9.6 ml). After 30 minutes the resulting suspension was diluted with water (15 ml) and the stirring was continued overnight. The solid was filtered off and washed with cold water.

After drying in the presence of KOH the product was crystallized from a mixture of methanol/acetonitrile=1:2.

Compound 43 was obtained (0.5 g; 17.2% yield) with m.p. 201°–203° C. (decomposition).

EXAMPLE 10

Preparation of N-[(1S,2R)-1-fluoromethyl-2-hydroxy-2-(4-methylsulfonylphenyl)ethyl]-benzenesulfonamide (Compound 44)

Benzenesulfonyl chloride (1.94 g; 11 mmol) was added at −5° C., in about one minute, to a solution of (1R,2S)-2-amino-3-fluoro-1-(4-methylsulfonylphenyl)-1-propanol hydrochloride (2.84 g; 10 mmol) in anhydrous pyridine (10 ml). The temperature was left to rise up to room value and the mixture was stirred overnight. It was poured into cold diluted HCl and extracted with ethyl acetate. The extracts washed with water and sodium bicarbonate were dried and evaporated to dryness. A crude (2.83 g) was obtained which was recrystallized from absolute ethanol (68 ml).

Compound 44 was obtained (1.83 g; 47.2% yield) with m.p. 184.5°–186.5° C.

By the same procedure, but using methanesulfonylchloride and ethanesulfonylchloride respectively, the compounds 45 and 46 reported in Table 1 were prepared.

EXAMPLE 11

Preparation of
N-[(1S,2R)-1-fluoromethyl-2-hydroxy-2-(4-methylsulfonylphenyl)ethyl]-chloromethanesulfonamide (Compound 47)

A mixture of (1R,2S)-2-amino-3-fluoro-1-(4-methylsulfonylphenyl)-1-propanol (2.48 g; 10 mmol), hexamethyldisilazane (1.62 g; 10 mmol) and tetrahydrofuran was refluxed for 6 hours.

After one night at room temperature it was treated at 50°–55° C. with sodium hydride (0.3 g; 10 mmol) (80% in vaseline) in small portions. After 2 hours it was cooled to −0° C. and a chloromethanesulfonyl chloride solution (1.51 g; 10 mmol) in tetrahydrofuran (5 ml) was added dropwise in 5 minutes.

Then the mixture was allowed to warm up to room temperature and after 1 hour was poured into water and ice, it was acidified and treated with ethyl acetate and tetrahydrofuran. The evaporated layers gave a dark oil which crystallized by treatment with dichloromethane.

A crystalline product were obtained which was recrystallized from ethyl acetate (35 ml).

Compound 47 (1.1 g; 30.6% yield) was thus obtained with m.p. 154°–156° C.

EXAMPLE 12

Preparation of dimethyl
N-[(1S,2R)-1-fluoromethyl-2-hydroxy-2-(4-methylsulfonylphenyl)ethyl]-phosphoroamidate
(Compound 48)

Dimethylchlorophosphate (1.44 g; 10 mmol) dissolved in dichloromethane (4 ml) was slowly added dropwise to a mixture cooled to 0° C. of (1R,2S)-2-amino-3-fluoro-1-(4-methylsulfonylphenyl)-1-propanol (2.47 g; 10 mmol) in acetonitrile (15 ml) and dichloroethane (15 ml) containing triethylamine (1.39 ml; 10 mmol).

After 1 hour the temperature was allowed to warm up to room temperature and it was left to rest for one night.

The solvent was evaporated and the residue collected with ethyl acetate and 5% diluted HCl. The phases were separated and the aqueous phase was extracted again.

The organic layers were washed up to neutrality, dried and evaporated. A crystalline solid was Obtained (0.67 g) which was purified by elution on silica gel with ethyl acetate/methanol=90:10: Compound 48 was obtained (0.4 g; 11.3% yield) with m.p. 153°–155° C. (decomposition).

EXAMPLE 13

Preparation of N-[(1S,2R)-1-fluoromethyl-2-hydroxy-2-(4-methylsulfonylphenyl)ethyl]-hydroxyiminoacetamide (Compound 49)

The compound 39 (prepared as described in example 6) (2.45 g; 6.5 mmol) and hydroxylamine hydrochloride (4.52 g; 6.5 mmol) in ethanol (30 ml) containing concentrate sulfuric acid (1 ml) were heated to reflux.

The alcohol was evaporated under vacuum and the residue was collected with water; it was washed with methylene chloride, salted with sodium chloride and extracted with tetrahydrofuran, the crude product was purified by chromatography on silica by eluting with dichloromethane/methanol=9:1.

Compound 49 was obtained (0.49 g; 23.7% yield) with m.p. 143°–145° C.

EXAMPLE 14

Preparation of N-[(1S,2R)-1-fluoromethyl-2-hydroxy-2-(4-methylsulfonylphenyl)ethyl]-2-hydroxyiminopropionamide (Compound 50)

The compound 100 (prepared as described in example 5) (4.2 g; 13.2 mmol) was added to hydroxylamine hydrochloride (1.04 g; 15 mmol), sodium acetate (1.23 g; 15 mmol) and water (8 ml), in ethanol (15 ml).

The mixture was heated to 85° C. for 1 hour, then the alcohol was evaporated under vacuum and the residue was collected with ethyl acetate. The organic phase was washed with water and dried under vacuum; a crystalline crude (2.7 g) was obtained which was recrystallized from dichloromethane/methanol.

Compound 50 was obtained (1.0 g; 22.8% yield) with m.p. 180°–182° C.

EXAMPLE 15

Preparation of
N-[(1S,2R)-1-fluoromethyl-2-hydroxy-2-(4-methylsulfonylphenyl)ethyl]-3-methoxyiminobutanamide (Compound 51)

A mixture of compound 42 (prepared as described in example 8) (2 g; 6 mmol), 0-methyl-hydroxylamine hydrochloride (0.58 g; 7 mmol) and sodium acetate (0.60 g; 7 mmol) in ethanol (25 ml), methanol (15 ml) and water (10 ml), was heated up to reflux temperature for 90 minutes.

The solvent was evaporated under vacuum and the residue was collected with ethyl acetate. It was washed with water and bicarbonate, dried and evaporated under vacuum. The oily residue was purified by chromatography on silica by eluting with dichloromethane/methanol=95:5.

Compound 51 was obtained (1.3 g; 60.1% yield) with m.p. 107°–109° C.

By the same method the compound 52 reported in Table 1 was prepared.

EXAMPLE 16

Preparation of
N-[(1S,2R)-1-fluoromethyl-2-hydroxy-2-
(4-methylsulfonyl)ethyl]-1H-tetrazol-1-acetamide
(Compound 53)

The compound 8 (prepared as described in example 1) (1.62 g; 5 mmol) and tetrazole containing 10% of water (0.47 g; 6 mmol), in 1N sodium hydroxide (6 ml) and ethanol (2 ml) were refluxed for 24 hours.

The solvent was evaporated and the residue was collected with tetrahydrofuran, washed with brine and diluted HCl.

The extracts evaporated to dryness gave the mixture of two regioisomers. The desired product was separated from its isomer by silica gel chromatography, eluent ethyl acetate/methanol=95:5.

Compound 53 (0.5 g; 28% yield) was obtained which decomposed above 70° C.

$^1$H-NMR (200 MHz) (DMSO-d$_6$): δ (ppm): 3.17 (s, 3H, CH$_3$SO$_2$); 4.18–4.77 (m, 3H, CH—CH$_2$F); 4.95 (m, 1H, CH—O); 5.10–5.30 (m, 2H, NHCOCH$_2$); 6.11 (d, 1H, J=4.4 Hz, OH); 7.61–7.87 (m, 4H, aromatics); 8.65 (d, 1H, J=8.6 Hz, NH); 9.20 (s, 1H, N—CH=N).

By the same procedure, but by using sodium azide, the compound 54 reported in Table 1 was prepared.

EXAMPLE 17

Preparation of
N-[(1S,2R)-1-fluoromethyl-2-hydroxy-2-
(4-methylsulfonylphenyl)ethyl]-oxamide
(Compound 55)

The compound 99 (prepared as described in example 3) (4.5g; 13 mmol) was dissolved in ethanol (20 ml) and was treated with a saturated ammonia solution in ethanol (45 ml).

After one night at room temperature the mixture was concentrated under vacuum and the residue was treated with petroleum ether, filtered and recrystallized from 75% aqueous ethanol.

Compound 55 was obtained (3.0 g; 72.5% yield) with m.p. 208°–210° C.

EXAMPLE 18

Preparation of
N-[(1S,2R)-1-fluoromethyl-2-hydroxy-2-
(4-methylsulfonylphenyl)ethyl]-oxamic acid
(compound 56)

A mixture of compound 99 (prepared as described in example 3) (2 g; 5,75 mmol) in ethanol (12.5 ml) was treated at room temperature with 1N sodium hydroxide (8.48 ml).

After 2 hours the alcohol was evaporated and the residue was diluted with water to obtain a solution, which was washed with ethyl ether, acidified at pH 1, saturated with sodium chloride and extracted with ethyl acetate.

After work-up, compound 56 (1.5 g; 81.7% yield) was obtained with m.p. 160°–162° C.

EXAMPLE 19

Preparation of
N-[(1S,2R)-1-fluoromethyl-2-hydroxy-2-
(4-methylsulfonylphenyl)ethyl]-2-hydroxyacetamide
(Compound 57)

Compound 17 (prepared as described in example 1) (2.27 g; 6.53 mmol) was suspended in ethanol at room temperature. 1N sodium hydroxide was added (6.53) and after 30 minutes the mixture was neutralized and evaporated to dryness.

The residue was collected with acetonitrile and the insoluble was filtered off; the filtrate was again evaporated to dryness and then crystallized from acetonitrile.

Compound 57 (1.1 g; 55.2% yield) was obtained with m.p. 160°–162° C.

EXAMPLE 20

Preparation of
N-[(1S,2R)-1-fluoromethyl-2-hydroxy-2-
(4-methylsulfonylphenyl)ethyl]-
2-methyl-sulfinylacetamide (Compound 58)

Hydrogen peroxide at 120 volumes (0.75 ml; 7.5 mmol) was added to a mixture cooled to 0° C. of compound 36 (prepared as described in example 5) (2 g; 5.96 mmol) in acetone (10 ml) and acetic acid (20 ml).

After 2.5 hours of stirring at room temperature the solution was concentrated under vacuum to dryness.

An oily residue was obtained which was purified by column chromatography, eluent dichloromethane/methanol=9:1.

Compound 58 (0.7 g, 33.4% yield) was obtained which was crystallized from ethyl acetate. M.p. 160°–161° C.

EXAMPLE 21

Preparation of
N-[(1S,2R)-1-fluoromethyl-2-hydroxy-2-
(4-methylsulfonylphenyl)ethyl]-2-
methylsulfonylacetamide (Compound 59)

Hydrogen peroxide at 130 volumes (3.2 ml; 42 mmol) was added drop-wise at 60° C. to a mixture of compound 36 (prepared as described in example 5) (2 g; 6 mmol) and Na$_2$WO$_4$·2H$_2$O (8.4 mg) in methanol (12 ml).

After 3 hours at 60° C. the heating was interrupted and it was left to rest for one night.

The solvent was evaporated to small volume and the resulting oil was chromatographed on silica gel by eluting with dichloromethane/ethanol=90:10.

The pure fractions were collected and evaporated to dryness, the product crystallized by treatment with tert.butylmethylether.

Compound 59 (1.6 g: 72.6% yield) was obtained with m.p. 167°–169° C.

EXAMPLE 22

Preparation of
(RS)-3-bromo-N-[(1S,2R)-1-fluoromethyl-
2-hydroxy-2-(4-methylsulfonylphenyl)ethyl]-
2-hydroxypropionamide (Compound 60) and
(RS)-2-bromo-N-[(1S,2R)-1-fluoromethyl-
2-hydroxy-2-(4-methylsulfonylphenyl)ethyl]-
3-hydroxypropionamide (Compound 61)

N-bromosuccinimide (4.10 g; 23 mmol) was added portionwise and in half an hour, at room temperature, to a suspension of compound 1 (prepared as described in example 1) (6,02 g; 20 mmol), in water (48 ml) and tert.butylalcohol (12 ml), acidified with 70% $HClO_4$ (0.3 ml).

After 18 hours of stirring the excess of the oxidant was reduced by sodium metabisulphite and the mixture was neutralized at pH 6 with sodium bicarbonate.

The alcohol was evaporated under vacuum and the residue was extracted with ethyl acetate and then washed with brine. After drying and evaporation of the solvent an oily residue was obtained which contained the two products and succinimide.

By chromatography on silica gel, eluent dichloromethane/methanol=9:1, the compound 60 (1.26 g; 15.8% yield) with m.p. 142°–144° C. was obtained and subsequently the other isomer as oil which crystallized from ethyl acetate: compound 61 (4.62 g; 58% yield) with m.p. 114°–116° C.

EXAMPLE 23

Preparation of
(RS)-N-[(1S,2R)-1-fluoromethyl-2-hydroxy-2-
(4-methylsulfonylphenyl)ethyl]-oxiranecarboxyamide
(Compound 62).

A solution of a mixture of isomeric compounds 60 and 61 (prepared as described in example 22) (8 g; 20 mmol) in tetrahydrofuran (75 ml) was added dropwise, in 45 minutes at room temperature, to a suspension of sodium hydride (80% in vaseline) (0.84 g; 28 mmol) in anhydrous tetrahydrofuran (75 ml).

After one night at room temperature the mixture was cooled with ice and treated with brine. The phases were separated and the aqueous phase was extracted again with ethyl acetate.

After drying and evaporation to dryness, a crude product (4.2 g) was obtained which was purified by chromatography on silica gel, eluent dichloromethane/methanol=95:5.

Compound 62 (3.2 g; 50.4% yield) was obtained with m.p. 132°–134° C.

EXAMPLE 24

Preparation of
(RS)-2,3-dihydroxy-N-[(1S,2R)-1-fluoromethyl-
2-hydroxy-2-(4-methylsulfonylphenyl)ethyl]-
propionamide (Compound 63)

Concentrated sulfuric acid (0.2 ml; 4 mmol) was added to a mixture of compound 62 (prepared as described in example 23) (1.27 g; 4 mmol) in acetone (2 ml) and water and the solution was heated to 50° C. for 5 hours.

It was then diluted with water and neutralized with sodium bicarbonate.

The acetone was evaporated and the mixture was acidified at pH 5–6 with HCl and extracted with tetrahydrofuran by salting the water with sodium chloride.

The dried obtained extracts (1.3 g) were purified by chromatography on silica gel by eluting with dichloroethane/methanol=85:15.

Compound 63 (0.743 g; 55.4% yield) was obtained which, after treatment with tert.butylmethylether showed m.p. 160°–162° C.

EXAMPLE 25

Preparation of
(S)-N-[(1S,2R)-1-fluoromethyl-2-hydroxy-2-
(4-methylsulfonylphenyl)ethyl]-2-
formylaminopropionamide (Compound 101)

Triethylamine (4.8 ml; 30 mmol), a solution of (1R,2S)-2-amino-3-fluoro- 1-(4-methylsulfonylphenyl)-1-propanol hydrochloride (8.51 g; 30 mmol) and triethylamine (4.18 ml) in methylene chloride (40 ml) and an N-hydroxybenzotriazole solution (13% of water) (4.66 g; 30 mmol) and again triethylamine (4.18 ml) in acetonitrile (45 ml) were added in sequence to a mixture of N-formylalanine (3.51 g; 30 mmol) in tetrahydrofuran.

The resulting mixture was cooled to 0° C. and treated with dicyclohexylcarbodiimide (6.19 g; 30 mmol) dissolved in acetonitrile (15 ml).

After 2 days stirring at room temperature the formed dicyclohexylurea was filtered off and the solvent was evaporated under vacuum.

The residue was collected with tetrahydrofuran and washed with brine alkalinized with $K_2CO_3$ at pH 8.5, then with brine acidified with HCl at pH 2 and finally up to neutrality. After evaporation of the solvent a residue (7 g) was obtained which was purified by chromatography on silica gel, eluent dichloromethane/methanol=9:1.

Compound 101 was obtained (4 g; 38.5% yield) with m.p. 139°–141° C.

EXAMPLE 26

Preparation of
(S)-2-amino-N-[(1S,2R)-1-fluoromethyl-
2-hydroxy-2-(4-methylsulfonylphenyl)ethyl]-
propionamide (Compound 64)

Method A

A mixture of compound 101 (prepared as described in example 25) (1.38 g: 4 mmol) in water (6 ml) and ethanol (3 ml) containing 85% hydrazine hydrate (0.707 g; 12 mmol) and glacial acetic acid (0.721 g; 12 mmol) was kept at 70° C. for 20 hours.

After evaporation of the ethanol, dilution with water and salting with $K_2CO_3$ the mixture was extracted several times with tetrahydrofuran. The extracts evaporated to dryness gave a product (1.25 g) which was purified by slow crystallization from isopropanol (3 ml). A product (0.55 g) was obtained which was further purified by silica gel chromatography by eluting with dichloromethane/methanol=85:5.

The product was treated with ethyl acetate/tert.butylmethylether thus affording the compound 64 (0.4 g; 31% yield) with m.p. 132°–134° C.

Method B

A mixture of compound 101 (prepared as described in example 25) (3.46 g; 10 mmol) in anhydrous methanol (20 ml) was treated with concentrated aqueous HCl (1 ml; 12 mmol).

After 90 hours at room temperature the alcohol was evaporated, the residue was collected with water, alkalinized with $K_2CO_3$ and extracted with tetrahydrofuran. The extracts after drying and evaporation of the solvent gave an oily product which crystallized from ethyl acetate/tert.butylmethylether.

Compound 64 (2.9 g; 91% yield) was obtained with the same characteristics as those of the product obtained by method A.

EXAMPLE 27

Preparation of
N-[(1R,2R)-2-hydroxy-1-hydroxymethyl-2-(4-methylthiophenyl)ethyl]-carbamate (Compound 65)

(1R,2R)-2-Amino-1-(4-methylthiophenyl)-1,3-propanediol (42.6 g; 0.2 mol) was suspended in ethyl acetate (1 l).

The suspension was cooled to 0° C. and 1N KOH (612 ml) was added.

A solution of ethyl chloroformate (22.8 g; 0.21 mol) in ethyl ether (230 ml) and 1N KOH (250 ml) were then contemporaneously added dropwise in such a way to keep the reaction temperature under 5° C. and the pH 7.5.

After 30 minutes the phases were separated and the organic phase was washed with 5% HCl, water, 5% $NaHCO_3$ and water in sequence. It was then dried over $Na_2SO_4$ and the solvent was evaporated. The oily residue was crystallized from 1,2-dichloroethane/diisopropylether= 2:3. Compound 65 (46 g; 80% yield) was obtained in a crystalline form with m.p. 73°–75° C.

By the same method the compounds 66 and 67, reported in Table 1, were prepared.

EXAMPLE 28

Preparation of
2,2-dichloro-N-[(1S,2R)-1-fluoromethyl-2-(4-methylsulfonylphenyl)-2-nitroxyethyl]-acetamide (Compound 68)

Fuming 90% nitric acid (63 ml) was cooled to −60° C. and the compound 34 (prepared as described in example 3) (13.6 g; 38 mmol) was suspended while the temperature was allowed to rise up to −45° C.

After 1 hour at such temperature a clear solution was obtained; then the temperature was slowly allowed to rise up to +10° C. in 2 hours.

The solution was poured into water and ice and the product was extracted with dichloromethane; the extracts were then washed to neutral pH, dried and concentrated under vacuum. A crude product (13.5 g) was obtained which was purified by silica gel chromatography by eluting with dichloromethane/methanol=95:5.

Compound 68 (8.4 g; 55% yield) was obtained as amorphous solid with softening point higher than 50° C.

$^1$H-NMR (200 MHz) (DMSO-$d_6$): δ (ppm): 3.21 (s, 3H, $CH_3SO_2$); 4.24–4.80 (m, 3H, CH—$CH_2$—F); 6.43 (d, 1H, J=5.3 Hz, CH—O); 6.44 (s, 1H, $CHCl_2$); 7.68–8.00 (m, 4H, aromatics); 9.19 (d, 1H, J=8.8 Hz, NH).

EXAMPLE 29

Preparation of
2,2-dichloro-N-[(S)-1-fluoromethyl-2-(4-methylsulfonylphenyl)- 2-oxoethyl]-acetamide (Compound 69)

A suspension of compound 34 (prepared as described in example 3) (10 g; 28 mmol), potassium bromate (4.67 g; 28 mmol) and cerium ammonium nitrate (1.53 g; 2.8 mmol) in acetonitrile (117 ml) and water (50 ml), was refluxed for 1 hour.

After one night rest, acetonitrile was evaporated under vacuum by replacing the distilled volume by water.

The mixture was cooled and the product was filtered and washed it with water. It was first crystallized from ethanol and then from acetonitrile.

Compound 69 (4.1 g; 41% yield) was obtained with m.p. 161°–163° C.

By the same method the compound 70, reported in Table 1, was prepared.

EXAMPLE 30

Preparation of
N-[(1S,2R)-2-acetoxy-1-fluoromethyl-2-(4-methylsulfonylphenyl)ethyl]-propenamide (Compound 71)

Acetic anhydride (1.06 ml; 10 mmol) was added dropwise, in 2 hours at room temperature, to a suspension of compound 1 (prepared as described in example 1) (1.5 g; 5 mmol) in acetonitrile (30 ml), containing triethylamine (2.10 ml; 15 mmol).

After 3 hours the mixture was evaporated under vacuum to dryness; the residue was collected with dichloromethane and water and the phases were separated. The organic phase, after drying and evaporation of the solvent, gave an amorphous residue (1.65 g) which was purified by silica gel chromatography, eluent dichloromethane/methanol=95:5.

Compound 71 (1.2 g; 70% yield) was obtained in a semi-crystalline form with m.p. 66°–70° C.

$^1$H-NMR (200 MHz) (DMSO-$d_6$): δ (ppm): 2.11 (s, 3H, $CH_3COO$); 3.20 (s, 3H, $CH_3SO_2$); 4.16–4.70 (m, 3H, CH—$CH_2$F); 5.60 (dd, 1H, $J_{cis}$=10 Hz, J=2.3 Hz, COCH=CH cis); 5.96 (d, 1H, J=5 Hz, CH—O); 6.01 (dd, 1H, $J_{trans}$=17 Hz, J=2.3 Hz, COCH=CH trans); 6.31 (dd, 1H, $J_{cis}$=10 Hz, $J_{trans}$=17 Hz, COCH=); 7,57–7.93 (m, 4H, aromatics); 8.41 (d, 1H, J=8.7 Hz, NH).

EXAMPLE 31

Preparation of 2-cyano-N-[(1R,2R)-2-hydroxy-2-(4-methylsulfonylphenyl)-1-methoxymethylethyl]-acetamide (Compound 72)

60% sodium hydride in oil (1.44 g) and anhydrous tetrahydrofuran (10 ml) were charged into a 500 ml three-necked flask equipped with reflux condenser, thermometer and dropping funnel and kept under inert atmosphere.

A mixture of (4R,5R)-4-hydroxymethyl-5-(4-methylthiophenyl)-2-phenyl-oxazoline in anhydrous tetrahydrofuran (270 ml) was added dropwise, the mixture was heated to 50°–600° C. for 1.5 hours then, after cooling at room temperature, methyl iodide (2.67 ml) dissolved in tetrahydrofuran (2.89 ml) was added dropwise.

The reaction mixture was stirred at room temperature for 3 hours then was poured into water and ice and was extracted with ethyl ether. The organic layers were dried with sodium sulfate and evaporated at reduced pressure to give (4R,5R)-5-(4-methylthiophenyl)-4-methoxymethyl-2-phenyl-2-oxazolidine.

The thus obtained product was dissolved in methanol (43 ml) and treated with sodium tungstate dihydrate (0.037 g) in water (0.8 ml).

The mixture was heated to 60° C. and 36% hydrogen peroxide (9.24 ml) was added dropwise, then the mixture was kept at this temperature for 8 hours.

By cooling at 5° C. an oil separated which was purified by silica gel chromatography, eluent ethyl acetate/hexane=7:3, to give (4R,5R)-5-(4-methylsulfonylphenyl)-4-methoxymethyl-2-phenyl-2-oxazoline (8.95 g).

The obtained product was treated with 20% hydrochloric acid (74.8 ml) and reflux heated for 8 hours. At the end of the reaction the solution was washed with methylene chloride and concentrated under vacuum. (1R,2R)-2-amino-3-methoxy-1-(4-methylsulfonylphenyl)-1-propanol (6 g) was obtained.

The obtained product was treated with methyl cyanoacetate (4.41 ml) and triethylamine (2.78 ml) at 100° C. for 8 hours.

After work-up the obtained crude was purified by silica gel chromatography, eluent methylene chloride/methanol= 97.5:2.5, to give compound 72 (0.49 g) as white solid, m.p. 152° C.

By the same method the compound 73, reported in Table 1, war prepared starting from (4R)-4-[(1R)-1-hydroxy-1-(4-methylthiophenyl)]-methyl-2-phenyl-2-oxazoline.

EXAMPLE 32

Preparation of
(1RS,2RS)-2-cyano-[1-ethyl-2-hydroxy-2-
(4-methylsulfinylphenyl)ethyl]-acetamide
(Compound 74)

Compound 29 (prepared as described in example 3) (0.55 g) and acetone (3 ml) were charged into a 25 ml three-necked flask equipped with thermometer, dropping funnel and magnetic stirrer.

A mixture formed by 36% hydrogen peroxide (0.6 ml) and glacial acetic acid (0.95 ml) was then added dropwise at the temperature of 30° C.

The reaction mixture was left at 30° C. for 3 hours.

At the end of the reaction the solvent was evaporated, the residue was collected with ethyl acetate, washed with a 5% sodium bicarbonate solution, dried over sodium sulfate and the solvent was evaporated.

The obtained crude was chromatographed on silica gel, eluent methylene chloride/methanol=98:2, to give the compound 74 (0.15 g) as white solid.

$^1$H-NMR (acetone): δ (ppm): 0.9 (t, 3H, CH$_3$); 1.3–1.8 (m, 2H, CH$_2$); 2.7 (s, 3H, SOCH$_3$); 3.5 (s, 2H, CH$_2$CN); 3.8–4.2 (m, 1H, CH—N); 4.8–5.1 (m, 2H, CHOH, OH); 7.3–7.9 (m, 5H, aromatics, NH).

By the same method but starting from compound 25 (prepared according to example 3) the compound 75, reported in Table 1, was prepared.

EXAMPLE 33

Preparation of
2-chloro-N-[(1R,2R)-2-hydroxy-1-hydroxymethyl-2-
(4-methylsulfonylphenyl)ethyl]-acetamide
(Compound 76)

The compound 66 (prepared as described in example 27) (14.5 g; 0.5 mol) was slowly added to hydrogen peroxide at 130 volumes (18.5 ml), at 40° C. At the end of the addition acetic anhydride (19.5 ml) was added dropwise, by keeping the reaction temperature between 35 and 45° C. The stirring was continued on for 20 hours while the mixture was slowly allowed to cool to room temperature. The precipitated product was filtered and washed carefully with water. Then it was recrystallized with ethanol.

Compound 76 (9.5 g; 59% yield) was obtained with m.p. 136°–138° C.

By the same method the compounds from 77 to 79 reported in Table 1 were prepared.

EXAMPLE 34

Preparation of
2,2-dichloro-N-[(1S,2S)-1-acetoxymethyl-2-hydroxy-
2-(4-methylthiophenyl)ethyl]-acetamide (Compound
80)

Acetyl chloride (5.84 ml; 82 mmol) was slowly added dropwise at a temperature between 0° and –5° C. to a mixture of compound 25 (prepared as described in example 3) (25 g; 77 mmol) in anhydrous pyridine (150 ml).

After 4 hours at 0° C. the mixture was poured into ice and concentrated HCl and extracted several times with dichloromethane. The combined extracts were then washed with water until neutral, dried and evaporated under vacuum. An oily residue (29 g) was obtained which crystallized from tert.butylmethylether.

The thus obtained compound 80 (18 g; 63.8% yield) had m.p. 100°–101° C.

By the same method the compounds from 81 to 88 reported in Table 1 were prepared.

NMR data of compound 81:

$^1$H-NMR (200 MHz) (DMSO-d$_6$): δ (ppm): 2.13 (s, 3H, CH$_3$COO); 3.23 (s, 3H, CH$_3$SO$_2$); 4.18–4.65 (m, 3H, CH—CH$_2$F); 5.98 (d, 1H, CH—O); 7,80 (q, 4H, aromatics); 8.02 (s, 1H, H—C=O); 8.50 (d, 1H, NH).

NMR data of compound 87 (the same as its enantiomer compound 88):

$^1$H-NMR (200 MHz) (DMSO-d$_6$): δ (ppm): 2.10 (s, 3H, CH$_3$COO); 3.18 (s, 3H, CH$_3$SO$_2$); 3.61 (s, 2H, CH$_2$CN); 4.14–4.64 (m, 3H, CH—CH$_2$F); 5.91 (d, 1H, J=4.3 Hz, CH—O); 7,58–7.91 (m, 4H, aromatics); 8.65 (d, 1H, J=8.6 Hz, NH).

EXAMPLE 35

Preparation of 2-chloro-N-[1(S)-1-acetoxymethyl-2-
(4-methylthiophenyl)-2-oxoethyl]-acetamide
(Compound 89)

A mixture of dimethylsulfoxide (8.11 ml; 114 mmol) in dichloromethane (8 ml) was slowly added dropwise to a solution of oxalyl chloride (4.58 ml; 54 mmol) in dichloromethane (8 ml) cooled to –70° C., by keeping the reaction temperature below −65° C. At the end of the addition a mixture of compound 83 (prepared as described in example 34) (15.8 g; 47.6 mmol) in dichloromethane (60 ml) was added dropwise, always at −70° C.

After 15 minutes triethylamine (16 ml; 115,4 mmol) diluted with dichloromethane (16 ml) was added dropwise in order to increase the pH of the solution to 7–7.5. The temperature was allowed to rise up to the room values, water was added and the phases were separated and the water phase was extracted again. The combined organic layers were then washed twice with 5% HCl and with water until neutral. After drying and evaporation of the solvent a crystalline residue (15 g) was obtained which was crystallized from acetonitrile/tert.butylmethyether=1:4.

Compound 89 (10.5 g; 67% yield) was obtained with m.p. 136°–138° C.

By the same method the compounds 90 and 91 reported in Table 1 were prepared.

EXAMPLE 36

Preparation of
N-[1(S)-1-acetoxymethyl-2-(4-methylsulfonylphenyl)-
2-oxoethyl]-acetamide (Compound 92)

The compound 79 (prepared as described in example 33) (107 g; 0.325 mol) in acetone (547 ml) and acetic acid (73 ml) was added dropwise in 30 minutes to a mixture of sodium dichromate dihydrated (129.4 g; 0.434 mol) in water (493 ml), acidified with concentrated sulfuric acid (164.2 ml) and kept at −3° C.

After 30 minutes the mixture was poured into water and ice and extracted three times with ethyl acetate. The extracts were then washed with water, with a solution of sodium metabisulfite and again with water, dried over sodium sulfate and evaporated to dryness to give a crystalline residue. The residue was purified by silica gel chromatography by eluting with dichloromethane/methanol from 99:1 to 97:3.

A product (77 g) was obtained which was crystallized from acetonitrile/tert.butylmethylether=1:2 to give compound 92 (43 g; 40.4% yield) with m.p. 129°–131° C.

EXAMPLE 37

Preparation of 2-cyano-N-[2-hydroxy-1-methyl-2-
(4-methylsulfonylphenyl)ethyl]-acetamide
(Compound 93) as mixtures of (1R,2R) and (1S,2S)
isomers.

Intermediate 2 (as mixture of threo and erythro isomers; prepared as described in example 2) (8 g), ethyl benzymidate hydrochloride (9.3 g) and methylene chloride (80 ml) were charged into a 250 ml three-necked flask equipped with thermometer and dropping funnel.

The mixture was cooled to 0° C. and pyridine (4 ml) was slowly added dropwise.

The reaction mixture was stirred at room temperature for two days.

At the end of the reaction the mixture was poured into water and ice, was acidified to pH 4 and extracted with methylene chloride.

The organic layers were dried over sodium sulfate and evaporated at reduced pressure.

A crude product (7.4 g) was obtained which was chromatographed on silica gel by eluting with methylene chloride to give (±)trans-4-methyl-5-(4-methylthiophenyl)-2-phenyl-2-oxazoline (3 g) and (±)cis-4-methyl-5-(4-methylthiophenyl)-2-phenyl-oxazoline (1.6 g) (±)Trans-4-methyl-5-(4-methylthiophenyl)-2-phenyl-2-oxazoline (3 g) dissolved in methanol (20 ml) and sodium tungstate dihydrate (0.1 g) dissolved into water (0.5 ml) were charged into a 100 ml two-necked flask equipped with thermometer and reflux condenser. The mixture was heated to 60° C. and hydrogen peroxide (3 ml) was added dropwise.

The mixture was stirred at 60° C. for 4 hours.

At the end of the reaction the solvent was evaporated, the residue was collected with ethyl acetate and washed with water.

The organic layers were dried with sodium sulfate and concentrated under vacuum to give a crude product (3.5 g) which was hydrolized by treatment with 20% HCl (36 ml) at 108° C. for 4 hours.

At the end of the reaction the solution was washed with methylene chloride, then concentrated at reduced pressure.

The solid was collected with brine (50 ml) and made alkaline with ammonia. It was repeatedly extracted with ethyl acetate, dried over sodium sulfate and the solvent was evaporated.

2-Amino-1-(4-methylsulfonylphenyl)-1-propanol (1.9 g) was obtained as (1R,2R) and (1S,2S) isomers mixture. This product was reacted with ethyl cyanoacetate (2.2 ml) at 100° C. for 6 hours.

At the end of the reaction the residue was chromatographed on silica gel, eluent methylene chloride/methanol= 98:2, and then crystallized from anhydrous ethanol.

Compound 93 (1.6 g) was thus obtained with m.p. 190°–191° C.

By the same method the compound 94 (as 1R,2S and 1S,2R isomer mixtures) reported in Table 1 was prepared.

EXAMPLE 38

Preparation of
N-[1-(4-methylsulfonylbenzoyl)ethenyl]-acetamide
(Intermediate 6)

A mixture of the compound 92 (prepared as described in example 36) (37 g; 0.113 mol) in acetonitrile (370 ml) was treated at room temperature with triethylamine (18.5 ml) and left to react for 3 hours. The solution was then evaporated under vacuum, the residue was collected with dichloromethane and 5% HCl.

The organic phases were washed up to neutral pH, dried over sodium sulfate and evaporated under vacuum.

The crystalline residue was purified by crystallization from a mixture of 1,2-dichloromethane/tert.butylmethylether=1:2.

Intermediate 6 (18.5 g; 61%) was obtained with m.p. 117°–119° C.

By the same method but starting from compound 90 (prepared in example 35) N-[1-(4-methylthiobenzoyl)-ethenyl]-acetamide (Intermediate 7) was prepared—m.p. 121°–123° C.

EXAMPLE 39

Preparation of
2,2-dichloro-N-[1-(4-methylsulfonylbenzoyl)
ethenyl]-acetamide (Intermediate 8)

A mixture of compound 70 (prepared as described in example 29) (156 g; 0.44 mol) in anhydrous pyridine (1560 ml), cooled to −15° C., was treated with mesyl chloride (75 ml; 0.66 mol) and dichloromethane (256 ml) at such rate that the temperature never exceeded −13° C.

After 2 hours the temperature was allowed to rise to −5° C. and the whole was poured into ice and concentrated HCl.

The phases were then separated and the aqueous one was extracted 3 times. The extracts were then washed until neutral, dried and evaporated under vacuum.

The crystalline residue was purified by silica gel chromatography by eluting with dichloromethane/ethyl acetate=9:1 and recrystallized from acetonitrile/tert.butylmethylether= 1:3.

Intermediate 8 (15.1 g; 10.4% yield) was thus obtained with m.p. 123°–125° C.

EXAMPLE 40

Preparation of
N-[1(RS)-1-cyanomethyl-2-(4-methylthiophenyl)-
2-oxo-ethyl]-acetamide (Compound 95)

A suspension of the intermediate 7 (prepared as described in example 38) (70.6 g; 0.3 mol) in ethanol (740 ml) and acetic acid (18 g; 0.3 mol), heated at 45° C., was treated with potassium cyanide (39.07 g; 0.6 mol) dissolved in water (115 ml) over 15 minutes.

After 1 hour at 45° C. the suspension was diluted with cold water and filtered off. The precipitate after washing with water and drying in oven at 50° C. was crystallized from anhydrous ethanol.

Compound 95 (67.2 g; 85.4% yield) was obtained with m.p. 153°–155° C.

EXAMPLE 41

Preparation of
N-[1(RS)-1-acetylthiomethyl-2-(4-methylthiophenyl)-
2-oxoethyl]-acetamide (Compound 96)

A suspension of the intermediate 7 (prepared as described in example 38) (30 g; 0.1275 mol) in toluene (60 ml) and thioacetic acid (12.65 ml; 0.1785 mmol) was heated to 70° C. for 2.5 hours.

After cooling and dilution with hexane, the mixture was filtered off and the precipitate was washed with cold hexane.

The product was purified by silica gel chromatography by eluting with dichloromethane/methanol=95:5.

Compound 96 (20.4 g; 51.4% yield) was obtained with m.p. 121°–123° C.

EXAMPLE 42

Preparation of
N-[1(RS)-1-methyl-2-(4-methylsulfonylphenyl)-
2-oxo-ethyl]-acetamide (Compound 97)

A mixture of the intermediate 6 (prepared as described in example 38) (16.31 g; 61 mmol) containing acetonitrile (163 ml) and 5% palladium on barium sulfate (2 g), was stirred under a hydrogen atmosphere at 2 bar and 20° C., until uptake of gas ceased. The mixture was filtered, evaporated to dryness and purified by silica gel chromatography by eluting with dichloromethane/methanol=95:5.

Compound 97 (11.2 g; 41.6% yield) was obtained with m.p. 143°–145° C.

By the same method but starting from the intermediate 8 (prepared in example 39) compound 98 reported in Table 1 was prepared.

EXAMPLE 43

Determination of herbicidal activity

The herbicidal activity of the compounds of formula I was evaluated both against dicotyledons and mocotyledons and both in pre-emergence and post-emergence treatments.

In general, the compounds of formula I showed a higher herbicidal activity against dicotyledons even if some of them were very effective also against monocotyledons.

Always in general, the compounds of formula I showed to be more effective in the post-emergence treatments even if many of them showed also a good herbicidal activity in the pre-emergence treatments.

The evaluation tests were carried out according to the following operative procedures.

Small pots (top diameter=10 cm, height=10 cm) containing sandy soil were prepared.

In each of them one of the following weeds were seeded:

dicotyledons: *Stellaria media*$^{(A)}$, *Vigna sinesis*$^{(B)}$, *Ipomoea purpurea*$^{(C)}$, *Capsella bursa pastoris*$^{(D)}$;

monocotyledons: *Setaria glauca*$^{(E)}$, *Alopecurus mysuroides*$^{(F)}$.

Each pot was watered as much as necessary for a good germination of the seeds.

The pots were divided into three groups, each containing at least 5 pots for each weed.

The first group was not treated with any herbicide and was used as comparison (control).

The second group was treated one day after sowing with a water-acetone dispersion (20% v/v) of the compound undergoing testing at the dose corresponding to 2 kg/ha, in order to evaluate the herbicidal activity in pre-emergence.

The third group was treated fifteen days after sowing, i.e. when the weeds depending on the species reached 10–15 cm height, with a water-acetone dispersion (20% v/v) of the compound undergoing testing at a dose corresponding to 2 kg/ha, in order to evaluate the herbicidal activity in post-emergence.

All the pots were kept under observation in a conditioned room: temperature 15°–26°° C., relative humidity=60%, photoperiod=12 hours, light intensity=5000 lux.

The pots were uniformly watered every two days in order to ensure a humidity degree sufficient for a good growth of the weeds.

28 days after the treatment, the herbicidal activity was evaluated according to a scale of scores referring to the decreased growth of the treated plants in comparison with that of the untreated ones (control):

0=0–20% decrease of growth

1=21–40% decrease of growth

2=41–60% decrease of growth

3=61–80% decrease of growth

4=decrease of growth higher than 80% or death of the treated plant

Some results are reported in the following tables.

TABLE 2

| | | | | | | |
|---|---|---|---|---|---|---|
| Herbicidal activity$^{(a)}$ in preemergence at the dose of 2 kg/ha. | | | | | | |
| | Weed$^{(c)}$: | | | | | |
| Compound$^{(b)}$ | A | B | C | D | E | F |
| 1 | 4 | 3 | | 4 | | |
| 3 | 4 | 3 | 3 | | | |

TABLE 2-continued

Herbicidal activity[a] in preemergence at the dose of 2 kg/ha.

| Compound[b] | Weed[c]: A | B | C | D | E | F |
|---|---|---|---|---|---|---|
| 18 | 4 | 4 | 4 | 4 | 4 | 3 |

Notes to table 2:
[a]Each datum is the average of at least 5 tests
[b]The compound numbers are those reported in table 1
[c]The letters indicate the weeds as above reported.

TABLE 3

Herbicidal activity[a] in post emergence at the dose of 2 kg/ha.

| Compound[b] | Weed[c]: A | B | C | D | E | F |
|---|---|---|---|---|---|---|
| 1 | 4 | | 4 | 4 | | |
| 2 | | 3 | 4 | | | |
| 3 | 4 | 4 | 4 | | | |
| 4 | 4 | 4 | 4 | | | |
| 6 | 4 | 3 | 4 | | | |
| 9 | 4 | 4 | 4 | | | |
| 10 | 4 | 4 | 4 | | | |
| 11 | 4 | 4 | 4 | | | |
| 12 | 4 | 4 | 4 | | | |
| 14 | 4 | 2 | 4 | | | |
| 17 | 4 | 4 | 4 | | | |
| 18 | 4 | 4 | 4 | 4 | 4 | 4 |
| 22 | 4 | | 3 | | | |
| 34 | 4 | 4 | 4 | | 4 | 4 |
| 35 | 4 | 4 | 4 | | 4 | 4 |
| 38 | 4 | 4 | 4 | | | |
| 40 | 4 | 4 | 4 | 4 | 4 | 4 |
| 43 | 4 | 4 | 4 | | 4 | 4 |
| 45 | 4 | 4 | 4 | | 4 | 4 |
| 46 | | 3 | 3 | | | |
| 47 | 3 | 4 | 4 | | | |
| 49 | 4 | 4 | 4 | | | |
| 54 | 4 | 4 | 4 | | 4 | 3 |
| 57 | 4 | 4 | 4 | | 4 | 4 |
| 58 | 4 | 3 | 4 | | | |
| 63 | 3 | 4 | | | | |
| 68 | 4 | 4 | 4 | 4 | 4 | 4 |
| 69 | 4 | 4 | | | | |
| 71 | 4 | 4 | 3 | | | |
| 85 | 4 | | 3 | | | |
| 87 | 4 | 4 | 4 | | 4 | 4 |
| 98 | 4 | 4 | 4 | | | |

Notes to table 3:
[a]Each datum is the average of at least 5 tests
[b]The compound numbers are those reported in table 1
[c]The letters indicate the weeds as above reported.

What we claim is:

1. A composition for agricultural use containing as active ingredient a compound of formula

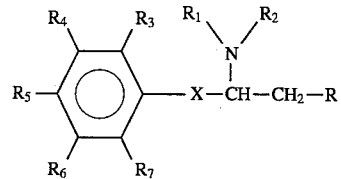

wherein

R is a hydrogen atom, alkyl, hydroxy, alkoxy, a fluorine, chlorine or bromine atom, a cyano group, alkylcarbonyloxy, alkylcarbonylthio, mercapto or alkylthio;

wherein one of $R_1$ and $R_2$ is a hydrogen atom or a $C_1$–$C_3$ alkyl and the other is a group $SO_2R_9$; $R_9$ is alkyl, mono or dichloroalkyl, phenyl optionally substituted by from 1 to 3 fluorine, chlorine of bromine atoms of alkyl; the $R_{10}$s are hydrogen atoms of alkyls;

$R_3$, $R_4$, $R_5$, $R_6$ and $R_7$, equal to of different from each other, each are a hydrogen, fluorine, chlorine or bromine atom, trifluoromethyl, alkyl, alkoxy, hydroxy, alkylthio, alkylsulfinyl, alkylsulfonyl, wherein alkyl is optionally substituted by from 1 to 3 fluorine, chlorine of bromine atoms; $C_2$–$C_6$ alkenylthio, benzylthio, $C_2$–$C_6$ alkenylsulfinyl, $C_2$–$C_6$ alkenylsulfonyl; benzylsulfinyl, benzylsulfonyl, benzenesulfonyl; cyano, alkylcarbonyl, alkylcarbonylamino; amino, mono or dialkylamino, trifluoroacetylamino, alkylsulfonylamino, benzoylamino wherein the phenyl may be substituted by from 1 to 3 substituents selected among fluorine, chlorine or bromine atoms or alkyls, or one of $R_3$, $R_4$, $R_5$, $R_6$ and $R_7$ is a phenyl, phenoxy, pyridyloxy, such groups being optionally substituted by from 1 to 3 substituents selected among fluorine, chlorine or bromine atoms, alkyl or alkoxy groups;

X is a

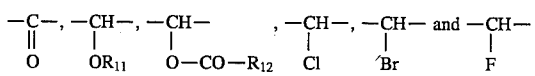

wherein $R_{11}$ is a hydrogen atom, alkyl, acyl of a mineral acid selected among nitric, phosphoric and sulfuric acid of an acyl of alkylsulfonic or benzenesulfonic acid; $R_{12}$ is an hydrogen atom, alkyl optionally substituted by from 1 to 3 substituents selected among fluorine, chlorine or bromine atoms, alkoxy or cyano; phenyl optionally substituted by from 1 to 3 substituents selected among fluorine, chlorine or bromine atoms, alkyl, nitro, alkoxy; a $C_2$–$C_6$ alkenyl;

and their salts with organic or inorganic acids compatible with agrarian use, and a carrier and optional additives of agricultural use.

2. A composition according to claim 1 in the form of dry powder, wettable powder, granulate, solution, suspension, emulsifiable concentrate and flowable.

3. A composition according to claim 1 for use in the defense of useful crops from weeds and a suitable carrier therefor.

4. A method for selectively controlling weeds in crop plants comprising applying thereto a herbicidally effective amount of a compound of the formula

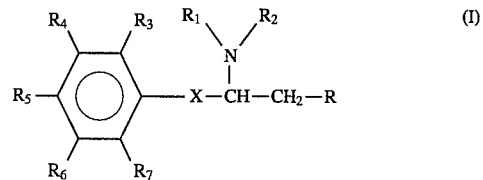

wherein

R is a hydrogen atom, alkyl, hydroxy, alkoxy, a fluorine, chlorine or bromine atom, a cyano group, alkylcarbonyloxy, alkylcarbonylthio, mercapto or alkylthio;

when one of $R_1$ and $R_2$ is a hydrogen atom or a $C_1$–$C_3$ alkyl the other group is a

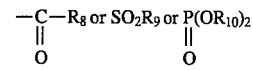

wherein $R_8$ is a hydrogen atom, alkoxy, aminocarbonyl, carboxy, alkoxycarbonyl, alkylcarbonyl, alkyl optionally substituted by from 1 to 3 substituents selected among fluorine, chlorine or bromine atoms, hydroxy, cyano, alkoxy, mercapto, $C_3$–$C_6$ cycloalkyl optionally substituted by 1 or 2 chlorine atoms, amino, mono or dialkylamino, formylamino, aminocarbonyl, alkylthio, alkylsulfinyl, alkylsulfonyl, hydroxyimino, alkoxyimino, carboxy, alkoxycarbonyl, alkylcarbonyloxy, tetrazolyl, alkylcarbonyl, phenyl and azido; $C_2$–$C_6$ alkylene optionally substituted by 1 or 2 fluorine or chlorine atoms or alkoxy; a $C_2$–$C_6$ alkynyl; a $C_3$–$C_6$ cycloalkyl; a heterocycle with 3–6 atoms among which 1 or 2 are heteroatoms selected among oxygen, nitrogen and sulfur; $R_9$ is alkyl, mono or dichloroalkyl, phenyl optionally substituted by from 1 to 3 fluorine, chlorine or bromine atoms or alkyl; and $R_{10}$ is a hydrogen atom or an alkyl group;

$R_3$, $R_4$, $R_5$, $R_6$ and $R_7$ equal to or different from each other, each are hydrogen, fluorine, chlorine or bromine atom, trifluoromethyl, alkyl, alkoxy, hydroxy, alkylthio, alkylsulfinyl, alkylsulfonyl, wherein alkyl is optionally substituted by from 1 to 3 fluorine, chlorine or bromine atoms; $C_2$–$C_6$ alkenylthio, benzylthio, $C_2$–$C_6$ alkenylsulfinyl, $C_2$–$C_6$ alkenylsulfonyl; benzylsulfinyl, benzylsulfonyl, benzenesulfonyl; cyano, alkylcarbonyl, alkylcarbonylamino; amino, mono or dialkylamino, trifluoroacetylamino, alkylsulfonylamino, benzoylamino wherein the phenyl may be substituted by from 1 to 3 substituents selected among fluorine, chlorine or bromine atoms or alkyl, or one of $R_3$, $R_4$, $R_5$, $R_6$, and $R_7$ is a phenyl, phenoxy, pyridyloxy, such groups being optionally substituted by from 1 to 3 substituents selected among fluorine, chlorine or bromine atoms, alkyl or alkoxy groups;

X is a

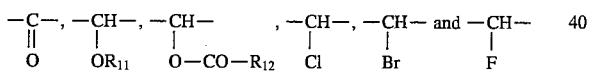

wherein $R_{11}$ is a hydrogen atom, alkyl, acyl of a mineral acid selected among nitric, phosphoric and sulfuric acid or an acyl of alkylsulfonic or benzenesulfonic acid; $R_{12}$ is a hydrogen atom, alkyl optionally substituted by from 1 to 3 substituents selected among fluorine, chlorine or bromine atoms, alkoxy or cyano; phenyl optionally substituted by from 1 to 3 substituents selected among fluorine, chlorine or bromine atoms, alkyl, nitro, alkoxy; a $C_2$–$C_6$ alkenyl;

and agriculturally acceptable salts and, optionally agriculturally acceptable carriers.

5. A method for the defense of useful crops according to claim 4 wherein the compound of formula I is distributed in an amount of from 0.03 to 6 kg/ha.

6. A method for the defense of useful crops according to claim 4 wherein the compound of formula I is distributed in the form of a composition suitable for agricultural use.

7. A method for the defense of useful crops according to claim 4 for the herbicidal treatment against dicotyledon weeds.

8. A method for selectively controlling weeds in crop plants comprising applying thereto a herbicidally effective amount of a compound of the formula

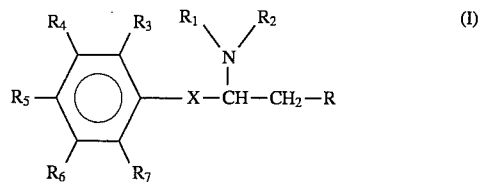

wherein

R is a hydrogen atom, alkyl, hydroxy, alkoxy, a fluorine, chlorine or bromine atom, a cyano group, alkylcarbonyloxy, alkylcarbonylthio, mercapto or alkylthio;

when one of $R_1$ and $R_2$ is a hydrogen atom or a $C_1$–$C_3$ alkyl the other group is a

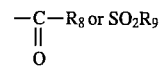

wherein $R_8$ is a hydrogen atom, alkoxy, aminocarbonyl, carboxy, alkoxycarbonyl, alkylcarbonyl, alkyl optionally substituted by from 1 to 3 substituents selected among fluorine, chlorine or bromine atoms, hydroxy, cyano, alkoxy, mercapto, $C_3$–$C_6$ cycloalkyl optionally substituted by 1 or 2 chlorine atoms, amino, mono or dialkylamino, formylamino, aminocarbonyl, alkylthio, alkylsulfinyl, alkylsulfonyl, hydroxyimino, alkoxyimino, carboxy, alkoxycarbonyl, alkylcarbonyloxy, tetrazolyl, alkylcarbonyl, phenyl and azido; $C_2$–$C_6$ alkylene optionally substituted by 1 or 2 fluorine or chlorine atoms or alkoxy; a $C_2$–$C_6$ alkynyl; a $C_3$–$C_6$ cycloalkyl; $R_9$ is alkyl, mono or dichloroalkyl, phenyl optionally substituted by from 1 to 3 fluorine, chlorine or bromine atoms or alkyl;

$R_3$, $R_4$, $R_5$, $R_6$ and $R_7$ equal to or different from each other, each are hydrogen, fluorine, chlorine or bromine atom, trifluoromethyl, alkyl, alkoxy, hydroxy, alkylthio, alkylsulfinyl, alkylsulfonyl, wherein alkyl is optionally substituted by from 1 to 3 fluorine, chlorine or bromine atoms; $C_2$–$C_6$ alkenylthio, benzylthio, $C_2$–$C_6$ alkenylsulfinyl, $C_2$–$C_6$ alkenylsulfonyl; benzylsulfinyl, benzylsulfonyl, benzenesulfonyl; cyano, alkylcarbonyl, alkylcarbonylamino; amino, mono or dialkylamino, trifluoroacetylamino, alkylsulfonylamino, benzoylamino wherein the phenyl may be substituted by from 1 to 3 substituents selected among fluorine, chlorine or bromine atoms or alkyl, or one of $R_3$, $R_4$, $R_5$, $R_6$, and $R_7$ is a phenyl, phenoxy, pyridyloxy, such groups being optionally substituted by from 1 to 3 substituents selected among fluorine, chlorine or bromine atoms, alkyl or alkoxy groups;

X is a

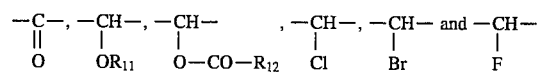

wherein $R_{11}$ is a hydrogen atom, alkyl, acyl of a mineral acid selected among nitric, phosphoric and sulfuric acid or an acyl of alkylsulfonic or benzenesulfonic acid; $R_{12}$ is a hydrogen atom, alkyl optionally substituted by from 1 to 3 substituents selected among fluorine, chlorine or bromine atoms, alkoxy or cyano; phenyl optionally substituted by from 1 to 3 substituents selected among fluorine, chlorine or bromine atoms, alkyl, nitro, alkoxy; a $C_2$–$C_6$ alkenyl;

and agriculturally acceptable salts and, optionally agriculturally acceptable carriers.

9. A method for the defense of useful crops according to claim 8 wherein the compound of formula I is distributed in an amount of from 0.03 to 6 kg/ha.

10. A method for the defense of useful crops according to claim 8 wherein the compound of formula I is distributed in the form of a composition suitable for agricultural use.

11. A method for the defense of useful crops according to claim 8 for the herbicidal treatment against dicotyledon weeds.

12. A method for the defense of useful crops according to claim 9 for the herbicidal treatment against dicotyledon weeds.

13. A method for the defense of useful crops according to claim 5 for the herbicidal treatment against dicotyledon weeds.

* * * * *